(12) United States Patent
Fukunaga et al.

(10) Patent No.: US 11,370,751 B2
(45) Date of Patent: Jun. 28, 2022

(54) SULFONIUM SALT, HEAT- OR PHOTO-ACID GENERATOR, HEAT- OR PHOTO-CURABLE COMPOSITION, AND CURED PRODUCT THEREOF

(71) Applicant: SAN APRO LTD., Kyoto (JP)

(72) Inventors: Noriya Fukunaga, Kyoto (JP); Yusaku Takashima, Kyoto (JP)

(73) Assignee: SAN APRO LTD., Kyoto (JP)

( * ) Notice: Subject to any disclaimer, the term of this patent is extended or adjusted under 35 U.S.C. 154(b) by 275 days.

(21) Appl. No.: 16/318,206

(22) PCT Filed: Jul. 6, 2017

(86) PCT No.: PCT/JP2017/024768
§ 371 (c)(1),
(2) Date: Jan. 16, 2019

(87) PCT Pub. No.: WO2018/020974
PCT Pub. Date: Feb. 1, 2018

(65) Prior Publication Data
US 2019/0284134 A1    Sep. 19, 2019

(30) Foreign Application Priority Data

Jul. 28, 2016 (JP) .............................. JP2016-148153

(51) Int. Cl.
*G03F 7/004* (2006.01)
*C07D 333/34* (2006.01)
(Continued)

(52) U.S. Cl.
CPC .......... *C07C 381/12* (2013.01); *C07D 209/88* (2013.01); *C07D 219/06* (2013.01); *C07D 279/20* (2013.01); *C07D 309/38* (2013.01); *C07D 311/16* (2013.01); *C07D 333/34* (2013.01); *C07D 333/76* (2013.01); *C07D 335/16* (2013.01); *C07D 339/08* (2013.01); *C07F 5/00* (2013.01); *C08G 59/68* (2013.01); *C09K 3/00* (2013.01); *G03F 7/0045* (2013.01);
(Continued)

(58) Field of Classification Search
CPC ........ G03F 7/0045; G03F 7/028; G03F 7/031; C07D 333/34; C07C 381/12
See application file for complete search history.

(56) References Cited

U.S. PATENT DOCUMENTS

| | | |
|---|---|---|
| 4,069,054 A | 1/1978 | Smith |
| 4,394,403 A | 7/1983 | Smith |

(Continued)

FOREIGN PATENT DOCUMENTS

| | | |
|---|---|---|
| CA | 1274646 A | 9/1990 |
| EP | 203829 A2 | 12/1986 |

(Continued)

OTHER PUBLICATIONS

English Translation of JP 2013014545 (Year: 2013).*
International Search Report dated Sep. 19, 2017, issued in counterpart application No. PCT/JP2017/024768 (3 pages).

*Primary Examiner* — Daborah Chacko-Davis
(74) *Attorney, Agent, or Firm* — Westerman, Hattori, Daniels & Adrian, LLP

(57) ABSTRACT

The sulfonium salt does not contain a toxic metal and exhibits higher cationic polymerization performance and crosslinking performance than a tetrakis(pentafluorophenyl) borate salt. The heat- or photo-acid generator contains the sulfonium salt. The sulfonium salt is formed of a sulfonium cation selected from a group represented by general formulas (1), (9), (10) and (11) described below and a gallate anion represented by formula (a). The heat- or photo-acid generator contains the sulfonium salt. The heat- or energy ray-curable composition contains the acid generator and a cationically polymerizable compound. A cured product can be obtained by curing the same.

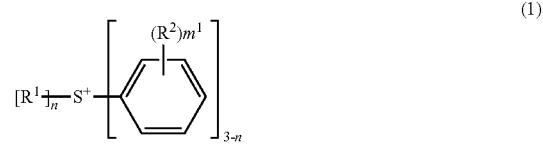

(1)

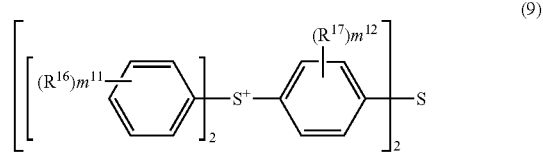

(9)

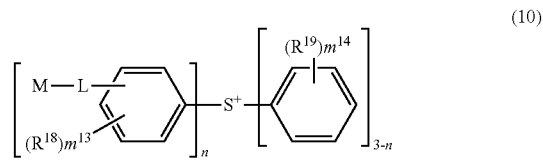

(10)

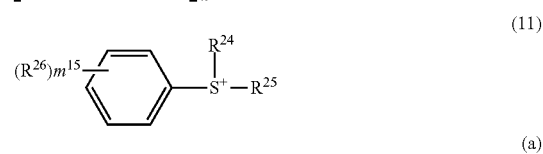

(11)

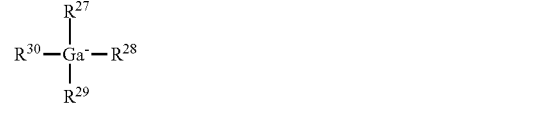

(a)

4 Claims, No Drawings

(51) Int. Cl.
*C07C 381/12* (2006.01)
*C07D 209/88* (2006.01)
*C07D 219/06* (2006.01)
*C07D 279/20* (2006.01)
*C07D 309/38* (2006.01)
*C07D 333/76* (2006.01)
*C07D 335/16* (2006.01)
*C07D 339/08* (2006.01)
*C07F 5/00* (2006.01)
*C07D 311/16* (2006.01)
*C09K 3/00* (2006.01)
*C08G 59/68* (2006.01)

(52) U.S. Cl.
CPC ...... *C07C 2603/18* (2017.05); *C07C 2603/24* (2017.05)

(56) References Cited

U.S. PATENT DOCUMENTS

| | | | |
|---|---|---|---|
| 4,450,360 A | 5/1984 | Crivello et al. | |
| 4,576,999 A | 3/1986 | Eckberg | |
| 4,640,967 A | 2/1987 | Eckberg | |
| 6,166,233 A | 12/2000 | Neckers et al. | |
| 10,683,266 B2 * | 6/2020 | Fukunaga | C07D 335/16 |
| 2002/0061405 A1 | 5/2002 | Malpert et al. | |
| 2009/0197987 A1 | 8/2009 | Hayoz et al. | |
| 2011/0039205 A1 * | 2/2011 | Suzuki | C08F 2/50 |
| | | | 430/270.1 |
| 2011/0300482 A1 * | 12/2011 | Suzuki | C08K 5/375 |
| | | | 430/270.1 |
| 2016/0083505 A1 | 3/2016 | Tanaka | |
| 2017/0305848 A1 * | 10/2017 | Shiota | G03F 7/0045 |
| 2019/0300476 A1 * | 10/2019 | Fukunaga | C08G 59/4064 |

FOREIGN PATENT DOCUMENTS

| | | | | |
|---|---|---|---|---|
| JP | 50-151997 A | | 12/1975 | |
| JP | 50-158680 A | | 12/1975 | |
| JP | 2-178303 A | | 7/1990 | |
| JP | 6-41215 A | | 2/1994 | |
| JP | 2000-66385 A | | 3/2000 | |
| JP | 2001-270990 A | | 10/2001 | |
| JP | 2001-294570 A | | 10/2001 | |
| JP | 2001-354669 A | | 12/2001 | |
| JP | 2002-193925 A | | 7/2002 | |
| JP | 2009-533377 A | | 9/2009 | |
| JP | 2012-56915 A | | 3/2012 | |
| JP | 2012-137741 A | | 7/2012 | |
| JP | 2013014545 | * | 1/2013 | ........... C07C 381/12 |
| JP | 2013-100237 A | | 5/2013 | |
| JP | 2014-224205 A | | 12/2014 | |
| WO | 2001-12720 A1 | | 2/2001 | |
| WO | 2005-116038 A1 | | 12/2005 | |
| WO | WO-2016047784 A1 * | | 3/2016 | ........... C07C 381/12 |

* cited by examiner

SULFONIUM SALT, HEAT- OR PHOTO-ACID GENERATOR, HEAT- OR PHOTO-CURABLE COMPOSITION, AND CURED PRODUCT THEREOF

TECHNICAL FIELD

The present invention firstly relates to a sulfonium salt, and secondly relates to a heat- or photo-acid generator containing a specific sulfonium salt suitable for curing a cationic polymerizable compound by the action of a heat or an active energy ray such as light, an electron beam, or an X-ray.

The present invention thirdly relates to a heat- or energy ray-curable composition for members that are required to have optical properties, the composition containing the heat- or photo-acid generator; and a cured product obtained by curing the same.

BACKGROUND ART

Onium salts such as iodonium and sulfonium salts have been heretofore known as cationic polymerization initiators for curing a cationic polymerizable compound such as an epoxy compound by application of heat or an active energy ray such as light or an electron beam (see Patent Documents 1 to 10).

In addition, since such an onium salt generates an acid by application of heat or an active energy ray, the onium salt is also referred to as an acid generator, and also used for resists and photosensitive materials (Patent Documents 11 to 13).

Incidentally, although cationic polymerization initiators (acid generators) described in these specifications contain $BF_4^-$, $PF_6^-$, $AsF_6^-$, or $SbF_6^-$ as an anion, curing performance of cationic polymerizable compound and crosslinking reaction performance varies with the kind of an anion and these performances are improved in an ascending order of $BF_4^- < PF_6^- < AsF_6^- < SbF_6^-$. However, applications of cationic polymerization initiators (acid generators) containing $AsF_6^-$ or $SbF_6^-$ which have good polymerization performance and crosslinking reaction performance are limited from a toxicity problem of As or Sb, and only a $SbF_6^-$ salt is used in a limited field such as photofabrication. On that account, although a $PF_6^-$ salt being poor in the polymerization performance and crosslinking reaction performance by acid catalyst is generally utilized, for example, in order to attain a curing rate almost comparable to that of a $SbF_6^-$ salt, since the $PF_6^-$ salt in an amount being nearly ten times the amount of the $SbF_6^-$ salt needs to be added and the remaining amount of an unreacted initiator (acid generator), a solvent used as necessary for dissolving the initiator (acid generator), or a decomposition product of the initiator is increased, there are problems that physical properties of a cured material are impaired, and moreover, a base material, facilities, and the like are liable to be corroded because of an increased amount of HF produced as a by-product by decomposition of the initiator. As such, a cationic polymerization initiator that is free from a toxic metal and has a cationic polymerization-initiating ability comparable to that of a $SbF_6^-$ salt has been strongly required.

In members that are required to have optical properties, such as displays, optical waveguides and optical lenses, importance is placed on transparency of cured products cured by application of heat or irradiation with an active energy ray such as light or an electron beam, and transparency of cured products after a heat resistance test and after a humidity resistance test. In addition, applications requiring corrosion resistance to a remaining strong acid include members such as paint compositions, coating agents, ink compositions, inkjet ink compositions, resist films, liquid resists, negative resists, MEMS resists, negative photosensitive materials, various adhesives, molding materials, casting materials, putty materials, glass fiber impregnating agents, fillers, sealing agents, sealants, optical semiconductor (LED) sealants, optical waveguide materials, nano-imprint materials, stereolithography materials, micro-stereolithography materials, and ACF (anisotropic conductive films).

The present inventors have proposed a fluorinated alkylphosphonic acid onium salt-based acid generator (Patent Document 14) as a cationic polymerization initiator (acid generator) which does not contain a toxic metal, and has cationic polymerization performance and crosslinking reaction performance comparable to those of a $SbF_6^-$ salt. However, a cured product including the acid generator has the problem that transparency is deteriorated particularly after a heat resistance test, and application of the acid generator to the above-mentioned members that are required to have optical properties has not progressed.

In addition, an onium salt having tetrakis(pentafluorophenyl)borate as an anion (Patent Document 15) is known as a cationic polymerization initiator (acid generator) which does not contain a toxic metal, and has cationic polymerization performance and crosslinking reaction performance comparable to those of a $SbF_6^-$ salt. However, a cured product including the acid generator has the problem that transparency is deteriorated because $HB(C_6F_5)_4$ as a strong acid remaining particularly after a heat resistance test causes corrosion and coloring of a resin etc., and application of the acid generator to the above-mentioned members that are required to have optical properties has not progressed.

PRIOR ART DOCUMENT

Patent Documents

Patent Document 1: Japanese Patent Application Laid-Open (JP-A) No. 50-151997
Patent Document 2: JP-A No. 50-158680
Patent Document 3: JP-A No. 02-178303
Patent Document 4: JP-A No. 02-178303
Patent Document 5: U.S. Pat. No. 4,069,054
Patent Document 6: U.S. Pat. No. 4,450,360
Patent Document 7: U.S. Pat. No. 4,576,999
Patent Document 8: U.S. Pat. No. 4,640,967
Patent Document 9: Canada Patent No. 1274646
Patent Document 10: European Patent Application Publication No. 203829
Patent Document 11: JP-A No. 2002-193925
Patent Document 12: JP-A No. 2001-354669
Patent Document 13: JP-A No. 2001-294570
Patent Document 14: WO2005-116038
Patent Document 15: JP-A No. 2000-66385

SUMMARY OF THE INVENTION

Problems to be Solved by the Invention

In view of the above-mentioned background, an object of the present invention is to provide a sulfonium salt which does not contain a toxic metal, has cationic polymerization performance and crosslinking reaction performance equivalent to or higher than those of tetrakis(pentafluorophenyl)borate salt; a heat- or photo-acid generator characterized in that said sulfonium salt is contained therein; a heat- or energy ray-curable composition including the heat- or photo-acid generator is capable of producing a cured product free from corrosion of members and free from the problem that transparency is deteriorated by corrosion of a resin because a strong acid does not remain particularly after a heat resistance test; and a cured product.

Solutions to the Problems

The present inventors have found a sulfonium salt [a heat- or photo-acid generator (hereinafter, in some cases, referred to as an acid generator)] suitable for the above-mentioned objects.

That is, the present invention provides a sulfonium salt formed of a sulfonium cation selected from a group represented by general formulas (1), (9), (10) and (11) described below and a gallate anion represented by formula (a); a heat- or photo-photoacid generator that is characterized in that said sulfonium salt is contained therein; a heat- or energy-ray curable composition containing said acid generator and a cationic polymerizable compound; and a cured product formed by curing these substances.

[Chemical Formula 1]

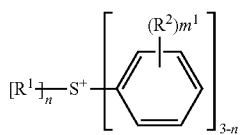

(1)

[in general formula (1), n represents an integer of 0 to 3; $R^1$ represents a group selected from formulas (2), (3), (4), (5) (6), (7) and (8); $R^2$ represents a hydrogen atom, an alkyl group, a hydroxy group, an alkoxy group, an alkylcarbonyl group, an arylcarbonyl group, an alkoxycarbonyl group, an aryloxycarbonyl group, an arylthiocarbonyl group, an acyloxy group, an arylthio group, an alkylthio group, an aryl group, a heterocyclic hydrocarbon group, an aryloxy group, an alkylsulfinyl group, an arylsulfinyl group, an alkylsulfonyl group, an arylsulfonyl group, a hydroxy(poly)alkyleneoxy group, an optionally substituted silyl group, an optionally substituted amino group, a cyano group, a nitro group, or a halogen atom; $m^1$ represents the number of occurrences of $R^2$; $m^1$ represents an integer of 0 to 5; $R^2$ may be the same or different from one another, and two or more $R^2$s may be linked together directly or through —O—, —S—, —SO—, —SO$_2$—, —NH—, —CO—, —COO—, —CONH—, an alkylene group or a phenylene group to form a ring structure including the element S.]

[Chemical Formula 2]

(2)

(3)

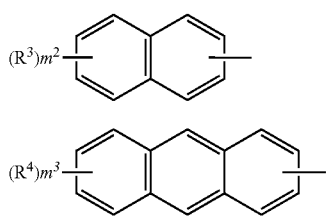

-continued (4)

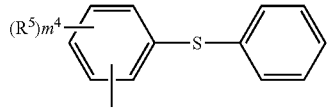

(5)

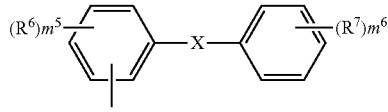

(6)

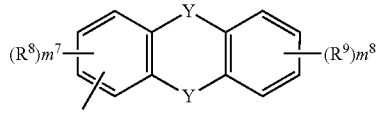

(7)

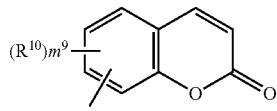

(8)

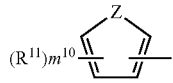

[in general formulas (2), (3), (4), (5), (6), (7) and (8), $R^3$ to $R^{11}$ each independently represent a hydrogen atom, an alkyl group, a hydroxy group, an alkoxy group, an alkylcarbonyl group, an arylcarbonyl group, an alkoxycarbonyl group, an aryloxycarbonyl group, an arylthiocarbonyl group, an acyloxy group, an arylthio group, an alkylthio group, an aryl group, a heterocyclic hydrocarbon group, an aryloxy group, an alkylsulfinyl group, an arylsulfinyl group, an alkylsulfonyl group, an arylsulfonyl group, a hydroxy(poly)alkyleneoxy group, an optionally substituted silyl group, an optionally substituted amino group, a cyano group, a nitro group, or a halogen atom; $m^2$ to $m^{10}$ each represent the number of occurrences of each of $R^3$ to $R^{11}$; $m^7$ and $m^{10}$ represent an integer of 0 to 3; $m^4$, $m^5$ and $m^8$ represent an integer of 0 to 4; $m^6$ and $m^9$ represent an integer of 0 to 5; $m^2$ represent an integer of 0 to 7; $m^3$ represent an integer of 0 to 9; $R^3$ to $R^{11}$ may be the same or different from one another; X represents —SO—, —SO$_2$—, —O—; Y represents a single bond, —S—, —SO—, —SO$_2$—, —O—, —CO—, —NR$^{12}$, CR$^{13}$R$^{14}$; Z represents —S—, —SO$_2$—, —O—, —NR$^{15}$; Y may be the same or different from one another; and $R^{12}$ to $R^{15}$ represent a hydrogen atom, an optionally substituted alkyl group having 1 to 18 carbon atoms, an optionally substituted aryl group having 6 to 20 carbon atoms or an optionally substituted aralkyl group having 7 to 20 carbon atoms.]

[Chemical Formula 3]

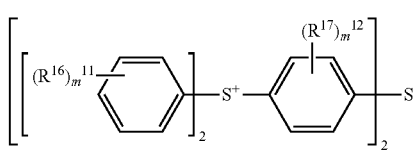

(9)

[in general formula (9), $R^{16}$ and $R^{17}$ represent a hydrogen atom, an alkyl group, a hydroxy group, an alkoxy group, an alkylcarbonyl group, an arylcarbonyl group, an alkoxycarbonyl group, an aryloxycarbonyl group, an arylthiocarbonyl group, an acyloxy group, an arylthio group, an alkylthio group, an aryl group, a heterocyclic hydrocarbon group, an aryloxy group, an alkylsulfinyl group, an arylsulfinyl group, an alkylsulfonyl group, an arylsulfonyl group, a hydroxy (poly)alkyleneoxy group, an optionally substituted silyl group, an optionally substituted amino group, a cyano group, a nitro group, or a halogen atom; $m^{11}$ and $m^{12}$ each represent the number of occurrences of each of $R^{16}$ and $R^{17}$; $m^{11}$ represents an integer of 0 to 5; $m^{12}$ represents an integer of 0 to 4; and $R^{16}$ and $R^{17}$ may be the same or different from one another.]

[Chemical Formula 4]

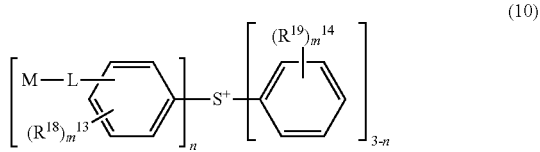

(10)

[in general formula (10), n represents an integer of 2 to 3; $R^{18}$ and $R^{19}$ represents a hydrogen atom, an alkyl group, a hydroxy group, an alkoxy group, an alkylcarbonyl group, an arylcarbonyl group, an alkoxycarbonyl group, an aryloxycarbonyl group, an arylthiocarbonyl group, an acyloxy group, an arylthio group, an alkylthio group, an aryl group, a heterocyclic hydrocarbon group, an aryloxy group, an alkylsulfinyl group, an arylsulfinyl group, an alkylsulfonyl group, an arylsulfonyl group, a hydroxy(poly)alkyleneoxy group, an optionally substituted silyl group, an optionally substituted amino group, a cyano group, a nitro group, or a halogen atom; $m^{13}$ and $m^{14}$ represent the number of occurrences of $R^{18}$ and $R^{19}$; $m^{13}$ represents an integer of 0 to 4; $m^{14}$ represents an integer of 0 to 5; $R^{18}$ and $R^{19}$ may be the same or different from one another; L represents a single bond, —S—, —O—, —NR$^{20}$, CR$^{21}$R$^{22}$, —NCOR$^{23}$; M represents an optionally substituted aryl group or an optionally substituted heterocyclic hydrocarbon group; two or more $R^{18}$s may be linked together directly or through —O—, —S—, —SO—, —SO$_2$—, —NH—, —CO—, —COO—, —CONH—, an alkylene group or a phenylene group to form a ring structure including the element S; and $R^{20}$ to $R^{23}$ represent a hydrogen atom, an optionally substituted alkyl group having 1 to 18 carbon atoms, an optionally substituted aryl group having 6 to 20 carbon atoms or an optionally substituted aralkyl group having 7 to 20 carbon atoms.]

[Chemical Formula 5]

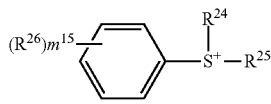

(11)

[in general formula (11), $R^{24}$ and $R^{25}$ represents an alkyl group or an aralkyl group; $R^{26}$ represents a hydrogen atom, an alkyl group, a hydroxy group, a carboxyl group, an alkoxy group, an aryloxy group, an alkylcarbonyl group, an arylcarbonyl group, an aralkylcarbonyl group, an alkoxycarbonyl group, an aryloxycarbonyl group, an aralkyloxycarbonyl group, an alkylcarbonyloxy group, an arylcarbonyloxy group, an aralkylcarbonyloxy group, an alkoxycarbonyloxy group, an aryloxycarbonyloxy group, an aralkyloxycarbonyloxy group, an arylthiocarbonyl group, an acyloxy group, an arylthio group, an alkylthio group, an aryl group, a heterocyclic hydrocarbon group, an aryloxy group, an alkylsulfinyl group, an arylsulfinyl group, an alkylsulfonyl group, an arylsulfonyl group, a hydroxy(poly)alkyleneoxy group, an optionally substituted silyl group, an optionally substituted amino group, a cyano group, a nitro group, or a halogen atom; $m^{15}$ represent the number of occurrences of $R^{26}$; $m^{15}$ represents an integer of 0 to 5; $R^{26}$ may be the same or different from one another; and two or more $R^{26}$s may be linked together directly or through —O—, —S—, —SO—, —SO$_2$—, —NH—, —CO—, —COO—, —CONH—, an alkylene group or a phenylene group to form a ring structure including the element S.]

[Chemical Formula 6]

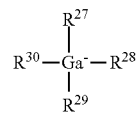

(a)

[in general formula (a), $R^{27}$ to $R^{30}$ each independently represent a phenyl group or a perfluoroalkyl group, and some of hydrogen atoms in these groups may be substituted with a group selected from a perfluoroalkyl group, a perfluoroalkoxy group, a nitro group, a cyano group, an acyl group and a halogen atom.]

Effects of the Invention

A sulfonium salt of the present invention which does not contain a toxic metal, has cationic polymerization performance and crosslinking reaction performance equivalent to or higher than those of tetrakis(pentafluorophenyl)borate salt.

The cured product of a heat- or energy ray-curable composition using the heat- or photo-acid generator containing the sulfonium salt is free from the problem of corrosion of members and free from the problem that transparency is deteriorated by corrosion of a resin because a strong acid does not remain particularly after a heat resistance test.

MODE FOR CARRYING OUT THE INVENTION

Hereinafter, embodiments of the invention are described in detail.

A sulfonium salt of the present invention is formed of a sulfonium cation selected from a group represented by general formulas (1), (9), (10) and (11) described below and a gallate anion represented by formula (a)

In formula (1), examples of the alkyl group for $R^2$ include straight chain alkyl groups having 1 to 18 carbon atoms (such as methyl, ethyl, n-propyl, n-butyl, n-pentyl, n-octyl, n-decyl, n-dodecyl, n-tetradecyl, n-hexadecyl, and n-octadecyl), branched chain alkyl groups having 3 to 18 carbon atoms (such as isopropyl, isobutyl, sec-butyl, tert-butyl, isopentyl, neopentyl, tert-pentyl, isohexyl, and isooctadecyl), and cycloalkyl groups having 3 to 18 carbon atoms (such as cyclopropyl, cyclobutyl, cyclopentyl, cyclohexyl, and 4-decylcyclohexyl).

In formula (1), examples of the alkoxy group for $R^2$ include straight chain alkoxy groups having 1 to 18 carbon atoms or branched chain alkoxy groups having 3 to 18 carbon atoms (such as methoxy, ethoxy, propoxy, isopropoxy, butoxy, isobutoxy, sec-butoxy, tert-butoxy, hexyloxy, decyloxy, dodecyloxy, and octadecyloxy).

In formula (1), examples of the alkylcarbonyl group for $R^2$ include straight alkylcarbonyl groups having 2 to 18 carbon atoms or branched chain alkylcarbonyl groups having 4 to 18 carbon atoms (such as acetyl, propionyl, butanoyl, 2-methylpropionyl, heptanoyl, 2-methylbutanoyl, 3-methylbutanoyl, octanoyl, decanoyl, dodecanoyl, and octadecanoyl).

In formula (1), examples of the arylcarbonyl group for $R^2$ include arylcarbonyl groups having 7 to 11 carbon atoms (such as benzoyl and naphthoyl).

In formula (1), examples of the alkoxycarbonyl group for $R^2$ include straight chain alkoxycarbonyl groups having 2 to 19 carbon atoms or branched chain alkoxycarbonyl groups having 4 to 19 carbon atoms (such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, octyloxycarbonyl, tetradecyloxycarbonyl, and octadecyloxycarbonyl).

In formula (1), examples of the aryloxycarbonyl group for $R^2$ include aryloxycarbonyl groups having 7 to 11 carbon atoms (such as phenoxycarbonyl and naphthoxycarbonyl).

In formula (1), examples of the arylthiocarbonyl group for $R^2$ include arylthiocarbonyl groups having 7 to 11 carbon atoms (such as phenylthiocarbonyl and naphthylthiocarbonyl)

In formula (1), examples of the acyloxy group for $R^2$ include straight chain acyloxy groups having 2 to 19 carbon atoms or branched chain acyloxy groups having 4 to 19 carbon atoms (such as acetoxy, ethylcarbonyloxy, propylcarbonyloxy, isopropylcarbonyloxy, butylcarbonyloxy, isobutylcarbonyloxy, sec-butylcarbonyloxy, tert-butylcarbonyloxy, octylcarbonyloxy, tetradecylcarbonyloxy, and octadecylcarbonyloxy).

In formula (1), examples of the arylthio group for $R^2$ include arylthio groups having 6 to 20 carbon atoms (such as phenylthio, 2-methylphenylthio, 3-methylphenylthio, 4-methylphenylthio, 2-chlorophenylthio, 3-chlorophenylthio, 4-chlorophenylthio, 2-bromophenylthio, 3-bromophenylthio, 4-bromophenylthio, 2-fluorophenylthio, 3-fluorophenylthio, 4-fluorophenylthio, 2-hydroxyphenylthio, 4-hydroxyphenylthio, 2-methoxyphenylthio, 4-methoxyphenylthio, 1-naphthylthio, 2-naphthylthio, 4-[4-(phenylthio)benzoyl]phenylthio, 4-[4-(phenylthio)phenoxy]phenylthio, 4-[4-(phenylthio)phenyl]phenylthio, 4-(phenylthio)phenylthio, 4-benzoylphenylthio, 4-benzoyl-2-chlorophenylthio, 4-benzoyl-3-chlorophenylthio, 4-benzoyl-3-methylthiophenylthio, 4-benzoyl-2-methylthiophenylthio, 4-(4-methylthiobenzoyl)phenylthio, 4-(2-methylthiobenzoyl)phenylthio, 4-(p-methylbenzoyl)phenylthio, 4-(p-ethylbenzoyl)phenylthio, 4-(p-isopropylbenzoyl) phenylthio, and 4-(p-tert-butylbenzoyl)phenylthio).

In formula (1), examples of the alkylthio group for $R^2$ include straight chain alkylthio groups having 1 to 18 carbon atoms or branched chain alkylthio groups having 3 to 18 carbon atoms (such as methylthio, ethylthio, propylthio, isopropylthio, butylthio, isobutylthio, sec-butylthio, tert-butylthio, pentylthio, isopentylthio, neopentylthio, tert-pentylthio, octylthio, decylthio, dodecylthio, and isooctadecylthio).

In formula (1), examples of the aryl group for $R^2$ include aryl groups having 6 to 10 carbon atoms (such as phenyl, tolyl, dimethylphenyl, and naphthyl).

In formula (1), examples of the heterocyclic hydrocarbon group for $R^2$ include heterocyclic hydrocarbon groups having 4 to 20 carbon atoms (such as thienyl, furanyl, pyranyl, pyrrolyl, oxazolyl, thiazolyl, pyridyl, pyrimidyl, pyrazinyl, indolyl, benzofuranyl, benzothienyl, quinolyl, isoquinolyl, quinoxalinyl, quinazolinyl, carbazolyl, acridinyl, phenothiazinyl, phenazinyl, xanthenyl, thianthrenyl, phenoxazinyl, phenoxathiinyl, chromanyl, isochromanyl, dibenzothienyl, xanthonyl, thioxanthonyl, and dibenzofuranyl).

In formula (1), examples of the aryloxy group for $R^2$ include aryloxy groups having 6 to 10 carbon atoms (such as phenoxy and naphthyloxy).

In formula (1), examples of the alkylsulfinyl group for $R^2$ include straight chain alkylsulfinyl groups having 1 to 18 carbon atoms or branched chain alkylsulfinyl groups having 3 to 18 carbon atoms (such as methylsulfinyl, ethylsulfinyl, propylsulfinyl, isopropylsulfinyl, butylsulfinyl, isobutylsulfinyl, sec-butylsulfinyl, tert-butylsulfinyl, pentylsulfinyl, isopentylsulfinyl, neopentylsulfinyl, tert-pentylsulfinyl, octylsulfinyl, and isooctadecylsulfinyl).

In formula (1), examples of the arylsulfinyl group for $R^2$ include arylsulfinyl groups having 6 to 10 carbon atoms (such as phenylsulfinyl, tolylsulfinyl, and naphthylsulfinyl).

In formula (1), examples of the alkylsulfonyl group for $R^2$ include straight chain alkylsulfonyl groups having 1 to 18 carbon atoms or branched chain alkylsulfonyl groups having 3 to 18 carbon atoms (such as methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, isopentylsulfonyl, neopentylsulfonyl, tert-pentylsulfonyl, octylsulfonyl, and octadecylsulfonyl).

In formula (1), examples of the arylsulfonyl group for $R^2$ include arylsulfonyl groups having 6 to 10 carbon atoms (such as phenylsulfonyl, tolylsulfonyl (tosyl group), and naphthylsulfonyl).

In formula (1), examples of the hydroxy(poly)alkyleneoxy group for $R^2$ include hydroxy(poly)alkyleneoxy groups represented by formula (12):

$$HO(-AO)q- \qquad (12)$$

[wherein AO represents an ethyleneoxy group and/or a propyleneoxy group, and q represents an integer of 1 to 5].

In formula (1), examples of the optionally substituted silyl group for $R^2$ include an silyl group and substituted silyl groups having 1 to 18 carbon atoms (such as methylsilyl, dimethylsilyl, trimethylsilyl, phenylsilyl, methylphenylsilyl, dimethylphenyldilyl, diphenylsilyl, diphenylmethylsilyl, and triphenylsilyl.)

In formula (1), examples of the optionally substituted amino group for $R^2$ include an amino group (—$NH_2$) and substituted amino groups having 1 to 15 carbon atoms (such as methylamino, dimethylamino, ethylamino, methylethylamino, diethylamino, n-propylamino, methyl-n-propylamino, ethyl-n-propylamino, n-propylamino, isopropylamino, isopropylmethylamino, isopropylethylamino, diisopropylamino, phenylamino, diphenylamino, methylphenylamino, ethylphenylamino, n-propylphenylamino, and isopropylphenylamino).

In formula (1), examples of the halogen atom for $R^2$ include a fluorine atom, a chlorine atom, a bromine atom, and an iodine atom.

In formula (1), $R^2$s are independent of one another and therefore may be the same as or different from one another.

$R^2$ preferably represents an alkyl group, a hydroxy group, an alkoxy group, and a halogen atom, and in particular, preferably represents a methyl group, a hydroxy group, a methoxy group, a chlorine atom, and a fluorine atom.

In formula (1), $m^1$ represents the number of occurrences of $R^2$ and $m^1$ represents an integer of 0 to 5, preferably 0 to 3, more preferably 0 to 2, in particular, preferably 0 or 1. When $m^1$ is in the preferred range, the sulfonium salt will have higher photosensitivity.

In general formulas (2) to (8), as $R^3$ to $R^{11}$, examples of the alkyl group, the alkoxy group, the alkylcarbonyl group, the arylcarbonyl group, the alkoxycarbonyl group, the aryloxycarbonyl group, the arylthiocarbonyl group, the acyloxy group, the arylthio group, the alkylthio group, the aryl group, the heterocyclic hydrocarbon group, the aryloxy group, the alkylsulfinyl group, the arylsulfinyl group, the alkylsulfonyl group, the arylsulfonyl group, the hydroxy (poly)alkyleneoxy group, the optionally substituted silyl group, the optionally substituted amino group, and the halogen atom are the same as those above-listed for $R^2$ in general formula (1).

In general formula (2) to (8), $R^3$ to $R^{11}$ are independent of one another and therefore may be the same as or different from one another.

In general formula (2) to (8), $R^3$ to $R^{11}$ preferably represent an alkyl group, a hydroxy group, an alkoxy group, an aryl group, an arylcarbonyl group, and a halogen atom, and in particular, preferably represents a methyl group, a hydroxy group, a methoxy group, a phenyl group, a phenyl carbonyl group, an acetyl group, and a bromine atom.

In general formula (2) to (8), $m^2$ to $m^{10}$ each represent the number of occurrences of each of $R^3$ to $R^{11}$ and $m^2$ represents an integer of 0 to 7, preferably 0 to 3, more preferably 0 to 2, in particular, preferably 0 or 1; $m^3$ represents an integer of 0 to 9, preferably 0 to 3, more preferably 0 to 2, in particular, preferably 0 or 1; $m^4$, $m^5$ and $m^8$ represent an integer of 0 to 4, preferably 0 to 3, more preferably 0 to 2, in particular, preferably 0 or 1; $m^6$ and $m^9$ represent an integer of 0 to 5, preferably 0 to 3, more preferably 0 to 2, in particular, preferably 0 or 1; $m^7$ and $m^{10}$ represent an integer of 0 to 3, preferably 0 to 2, in particular, preferably 0 or 1. When $m^2$ to $m^{10}$ are in the preferred range, the sulfonium salt will have higher photosensitivity.

In general formulas (2) to (8), examples of $R^{12}$ to $R^{15}$ for —$NR^{12}$, $CR^{13}R^{14}$, and —$NR^{15}$ of Y and Z include a hydrogen atom, an optionally substituted alkyl group having 1 to 18 carbon atoms (methyl, ethyl, n-propyl, isopropyl, n-buthyl, isobuthyl, sec-buthyl, tert-buthyl, n-penthyl, iso-penthyl, neopenthyl, tert-penthyl, isohexyl, n-octhyl, n-decyl, n-dodecyl, n-tetradecyl, n-hexadecyl, n-octadecyl, and isooctadecyl); an optionally substituted aryl group having 6 to 20 carbon atoms (phenyl, tolyl, 4-fluorophenyl, 4-hydroxyphenyl, and 4-methoxyphenyl); or an optionally substituted aralkyl group having 7 to 20 carbon atoms (benzyl, 2-methyl benzyl, 3-hydroxybenzyl, and 3-methoxybenzyl).

Preferred specific examples of the group represented by general formula (2) are shown below.

[Chemical Formula 7]

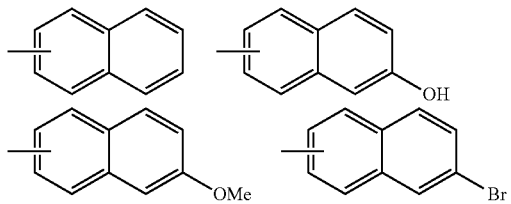

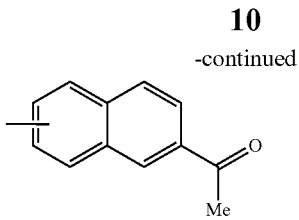

Preferred specific examples of the group represented by general formula (3) are shown below.

[Chemical Formula 8]

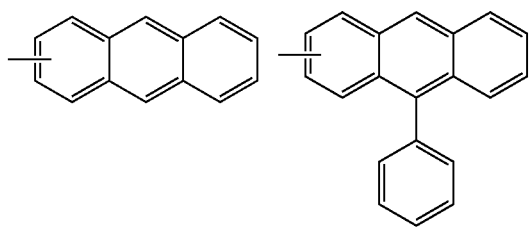

Preferred specific examples of the group represented by general formula (4) are shown below.

[Chemical Formula 9]

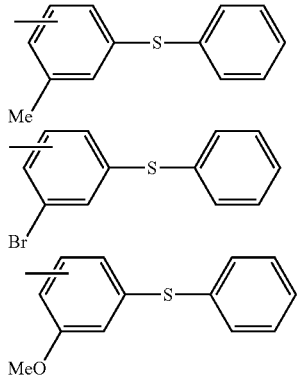

Preferred specific examples of the group represented by general formula (5) are shown below.

[Chemical Formula 10]

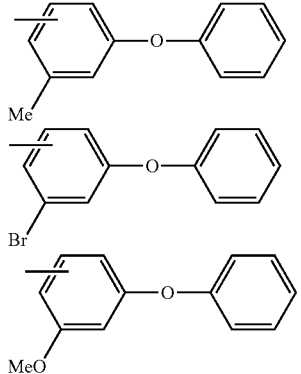

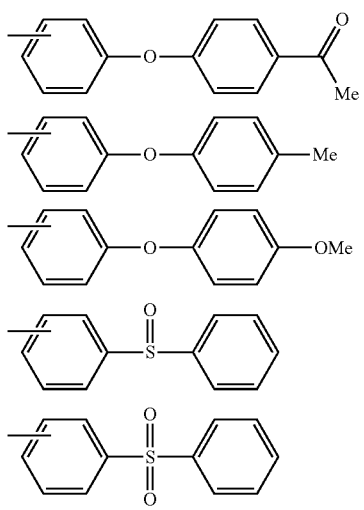
Preferred specific examples of the group represented by general formula (6) are shown below.
[Chemical Formula 11]
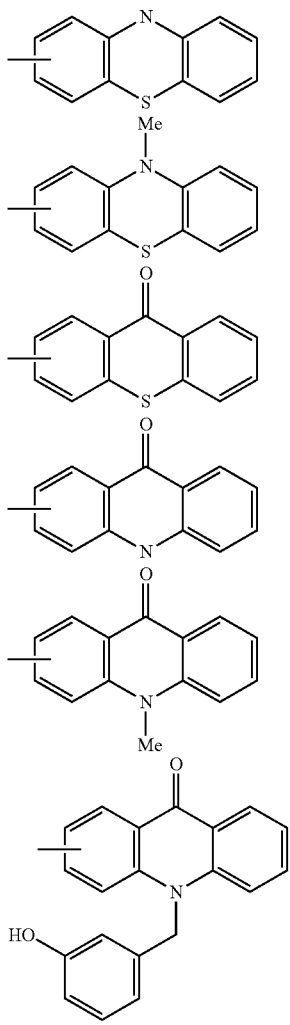
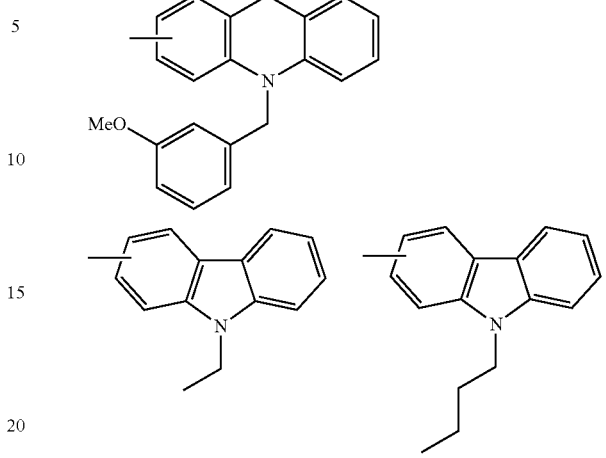
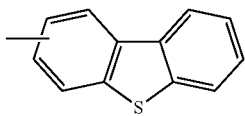
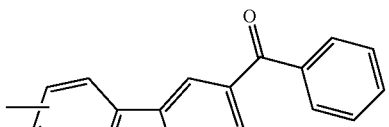
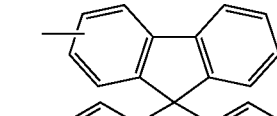
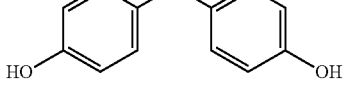
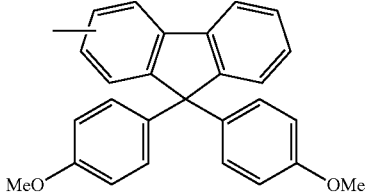
Preferred specific examples of the group represented by general formula (7) are shown below.
[Chemical Formula 12]
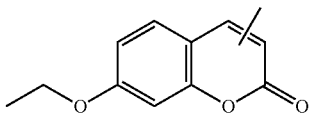
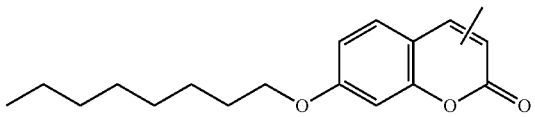

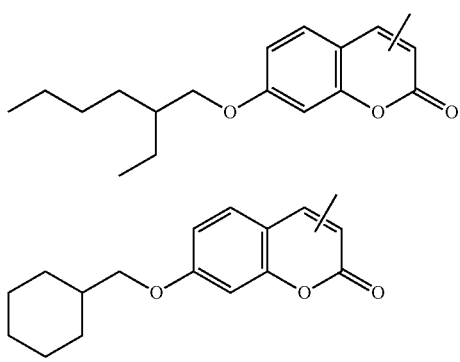

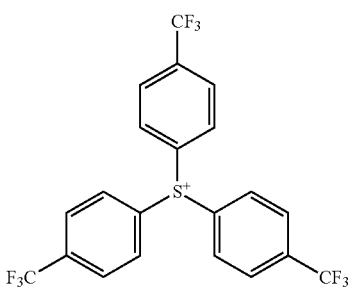

Preferred specific examples of the group represented by general formula (8) are shown below.

[Chemical Formula 13]

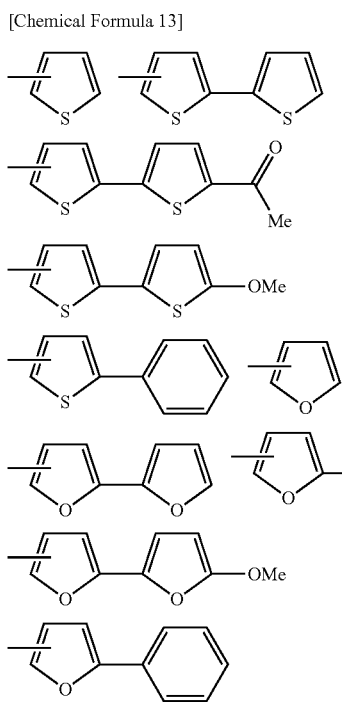

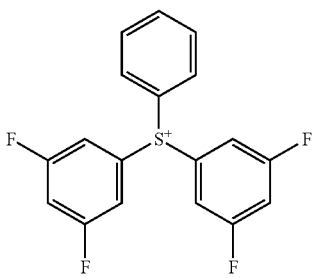

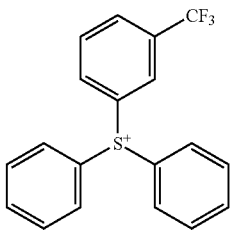

Preferred specific examples of the sulfonium cation represented by general formula (1) are shown below. In particular, preferred sulfonium cation is the cation having the group represented by formula (4) for $R^1$, in formula (1); having 1 for n; and having 0 for $m^4$, in formula (4).

[Chemical Formula 14]

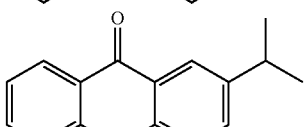

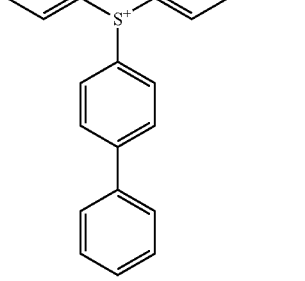

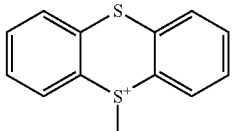

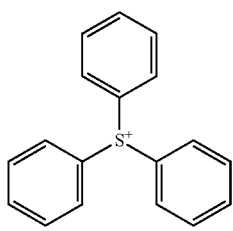

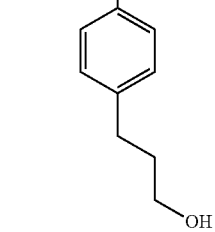

[Chemical Formula 15]
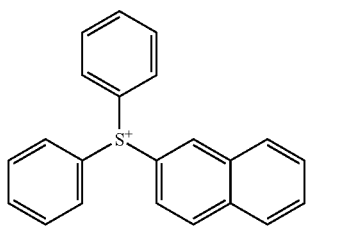
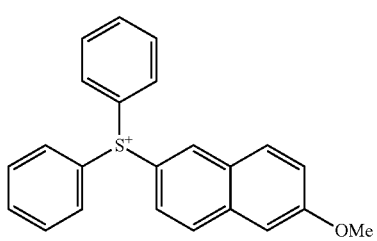
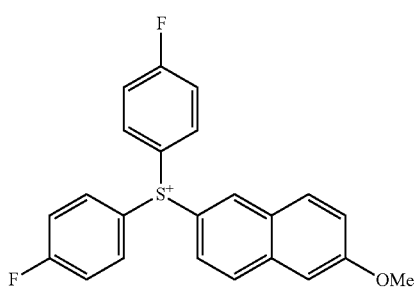
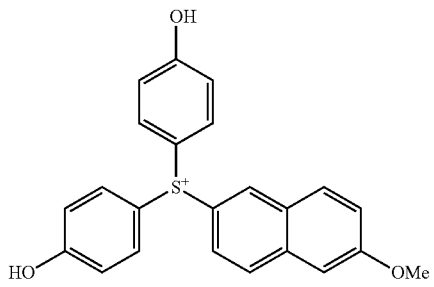
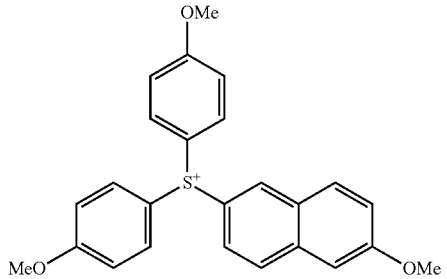
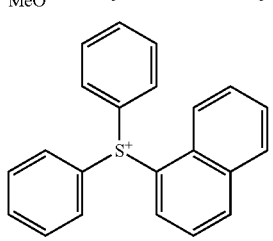
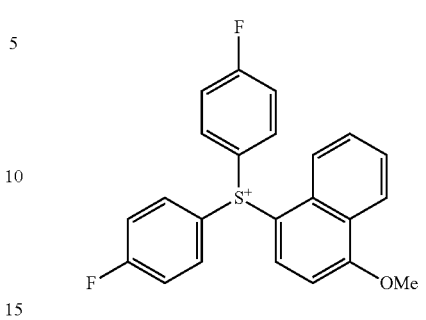
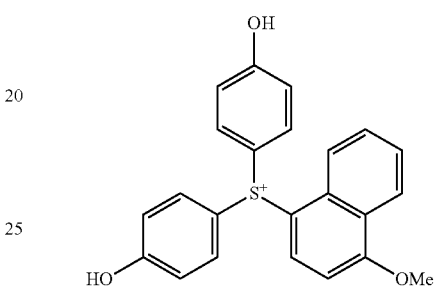
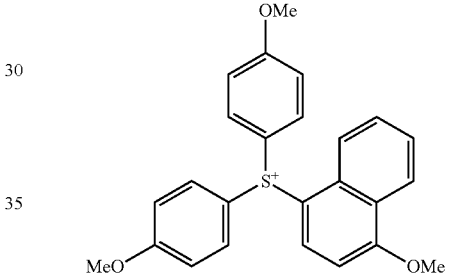
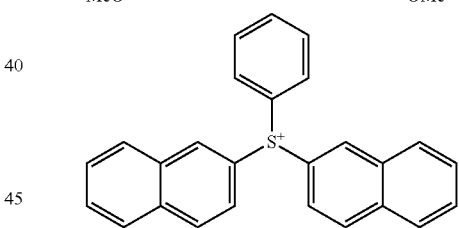
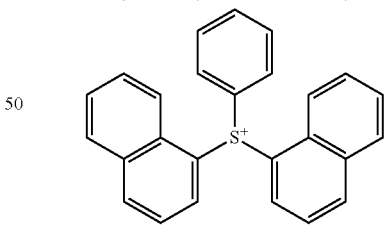
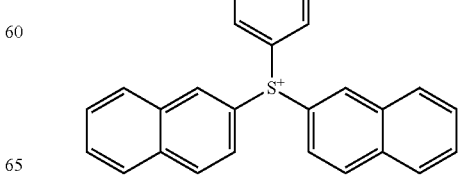

[Chemical Formula 16]
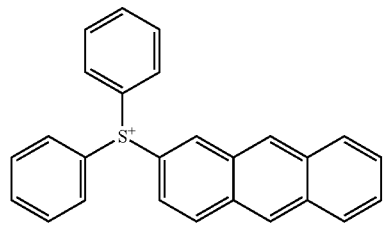
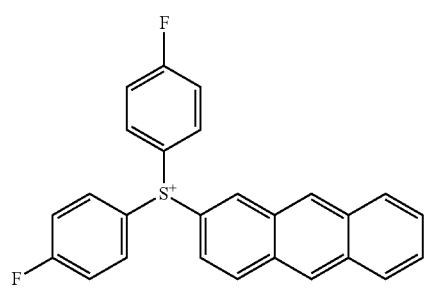
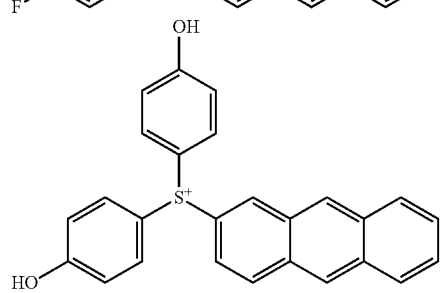
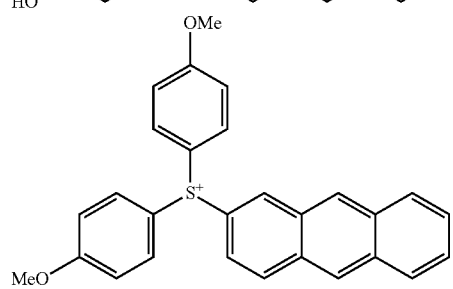
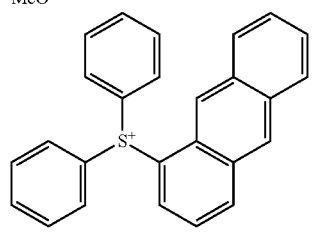
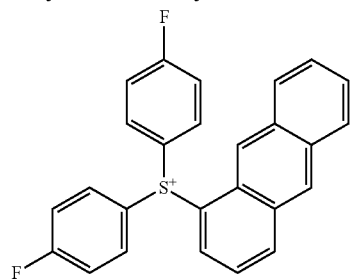
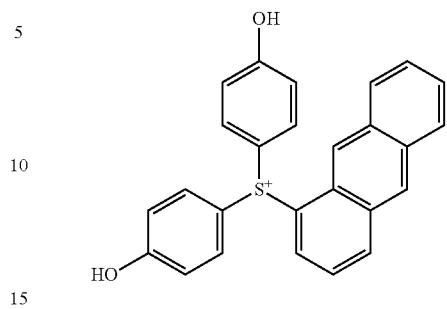
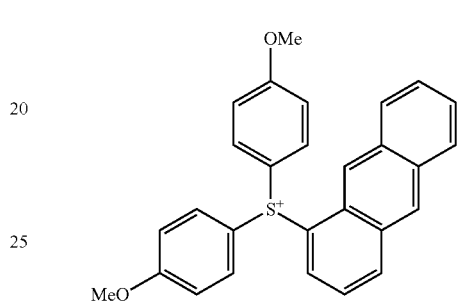
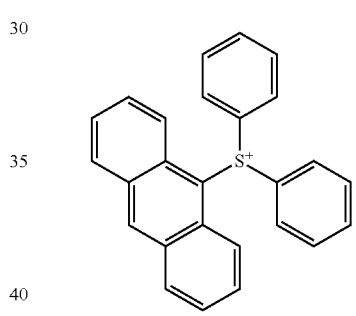
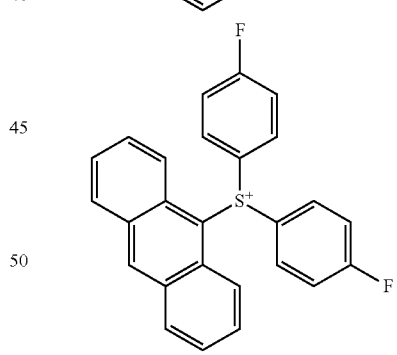
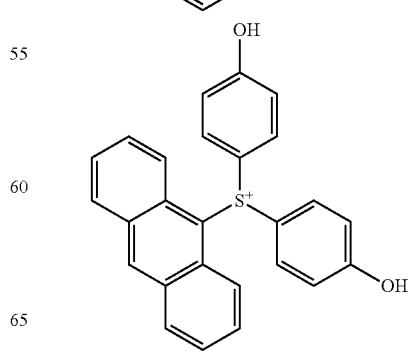

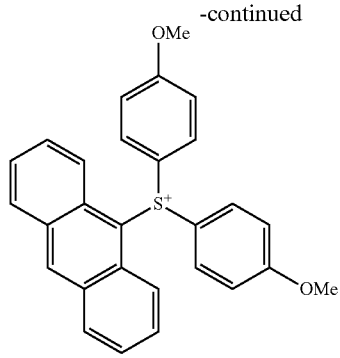
[Chemical Formula 17]
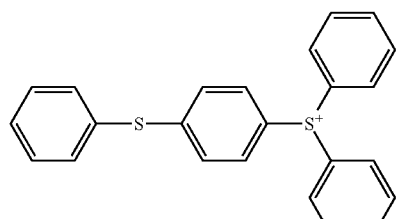
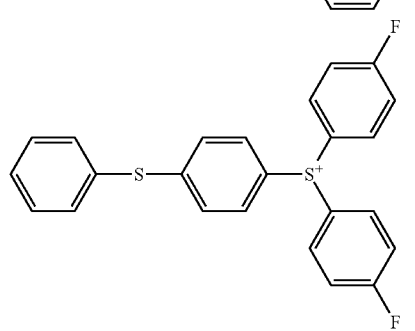
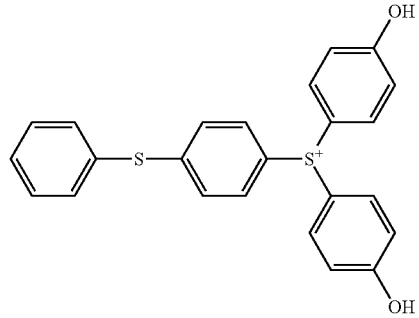
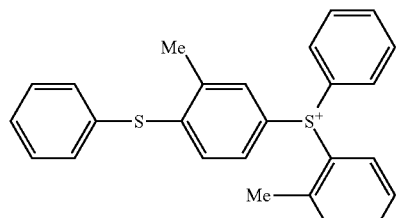
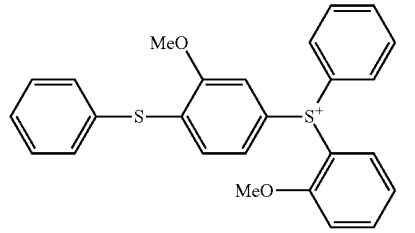
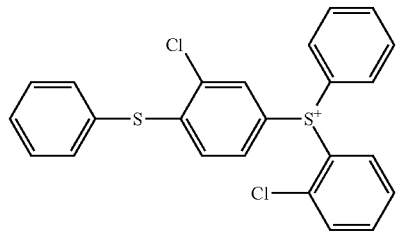
[Chemical Formula 18]
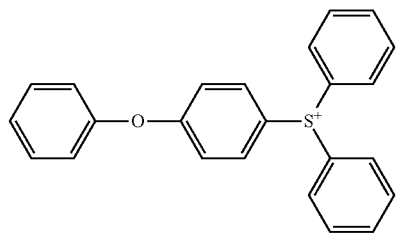
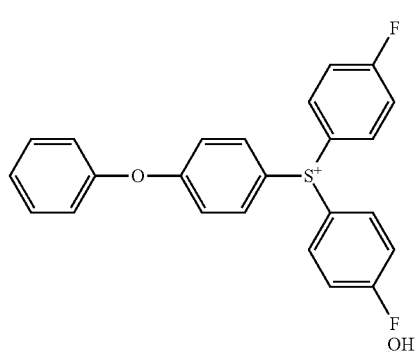
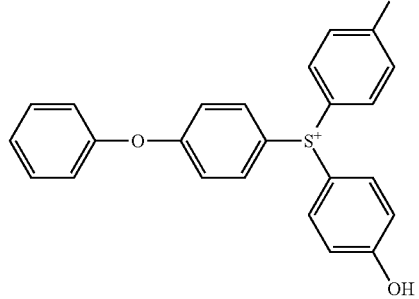
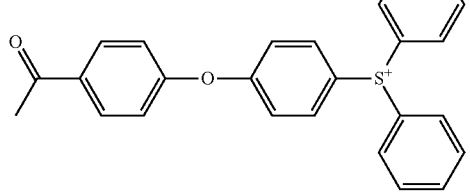
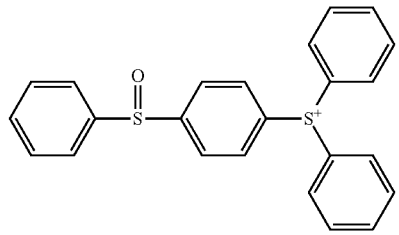

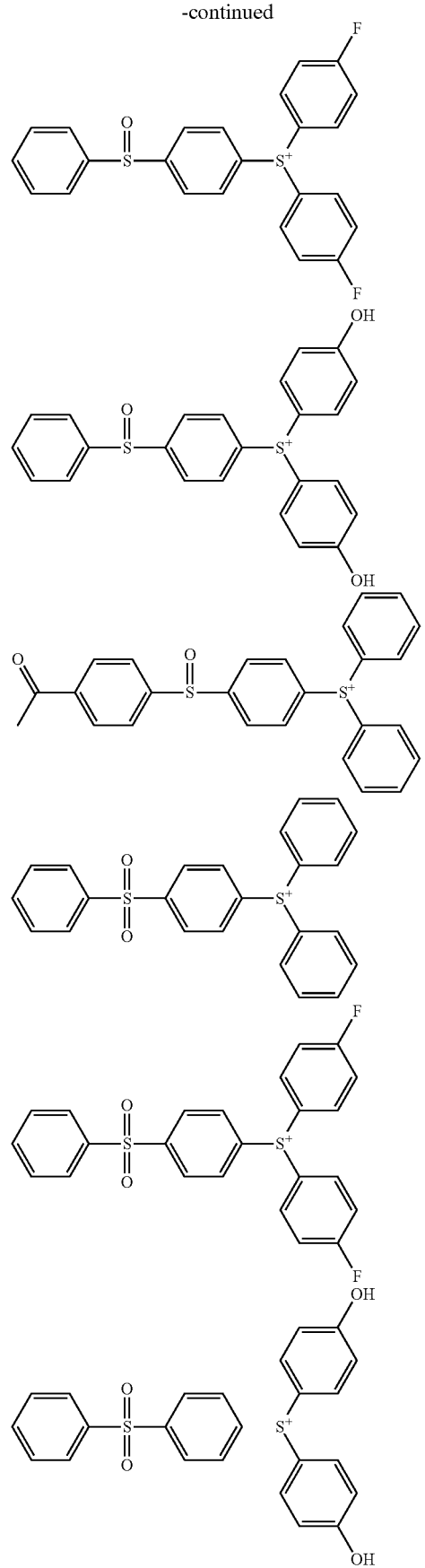
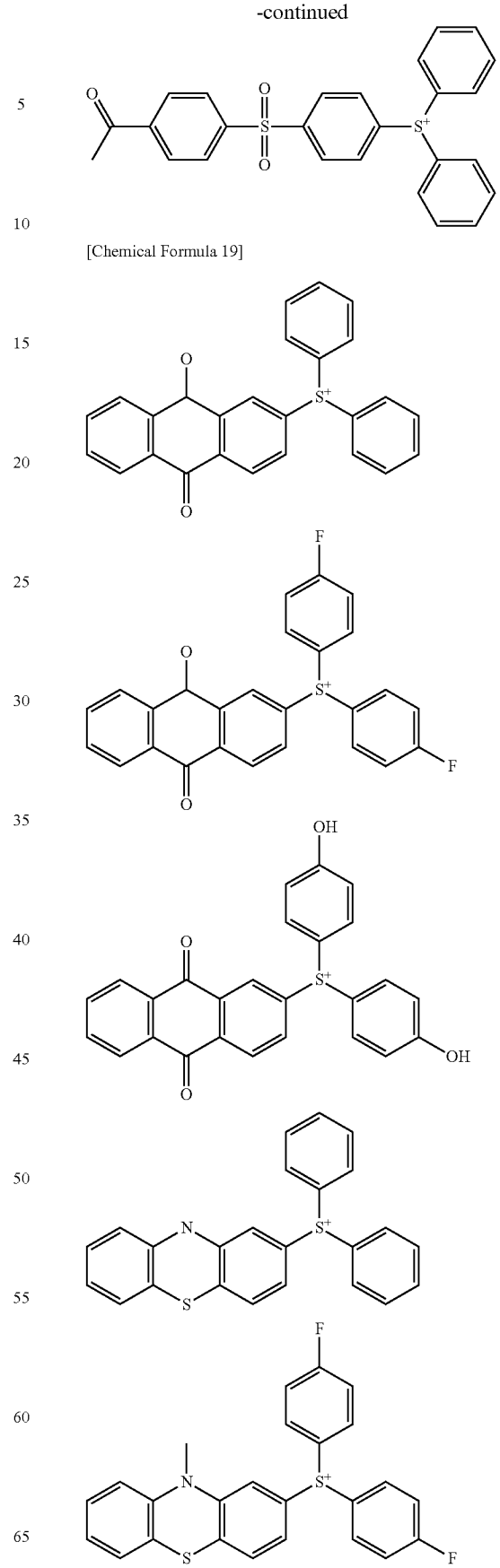
[Chemical Formula 19]

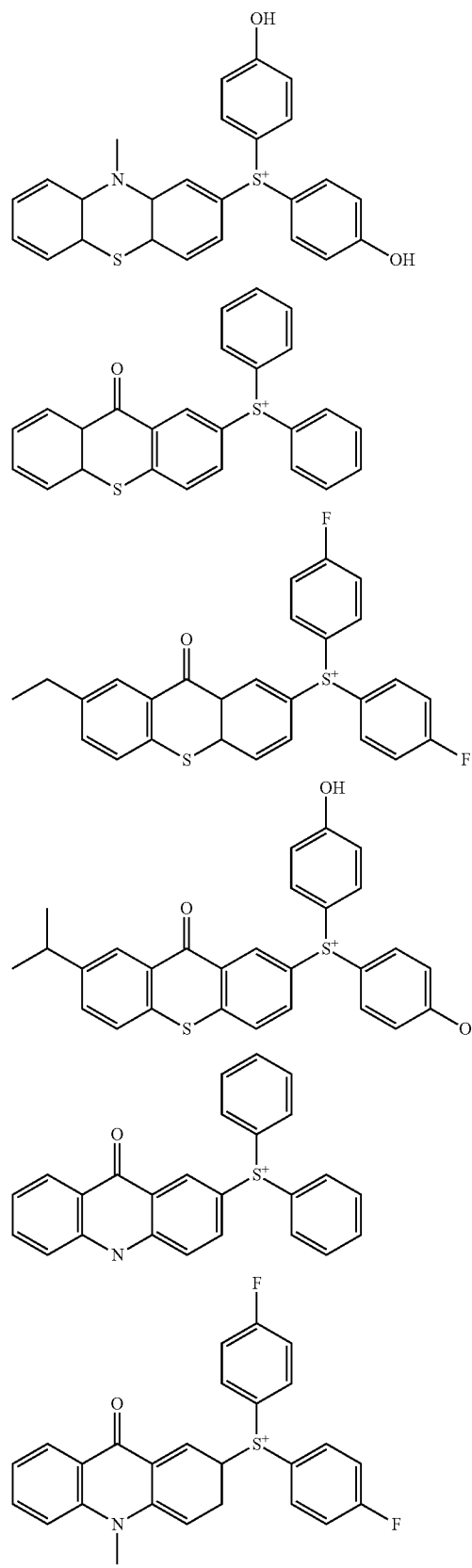
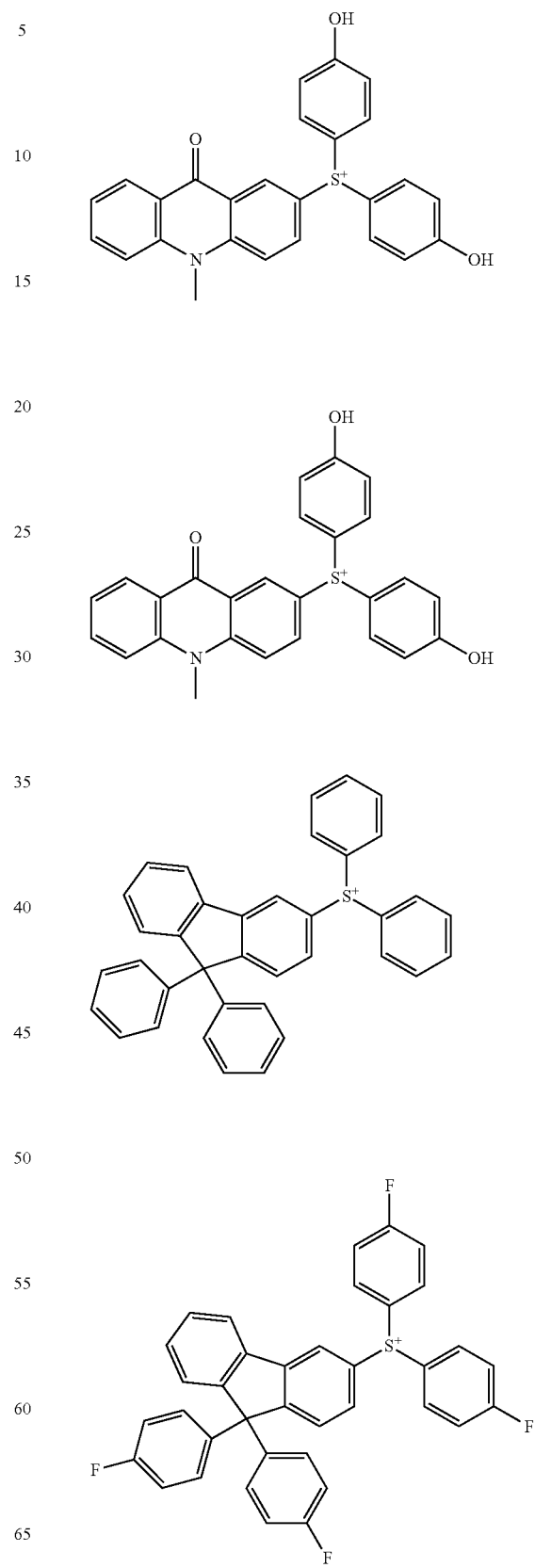

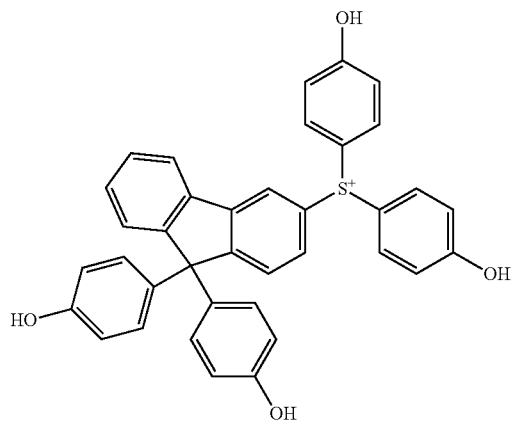
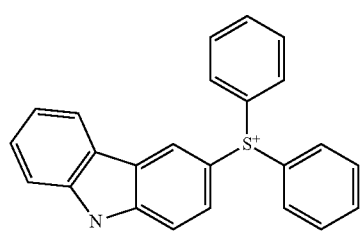
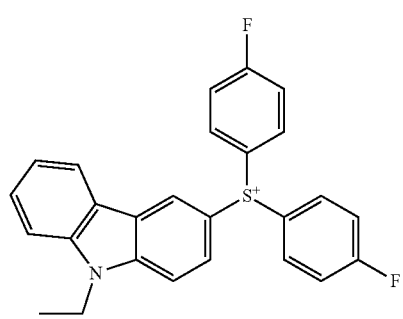
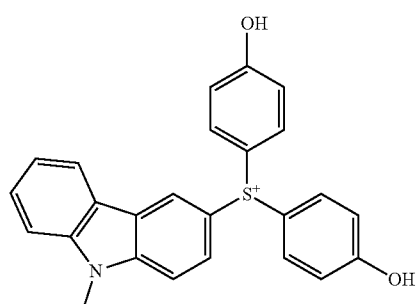
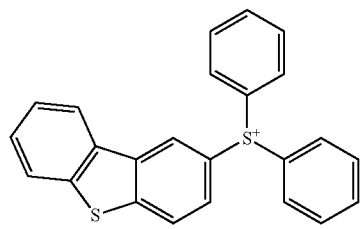
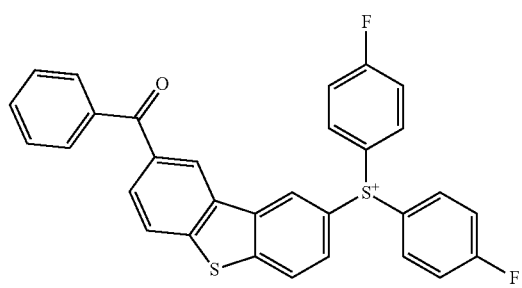
[Chemical Formula 20]
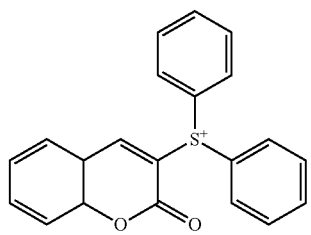
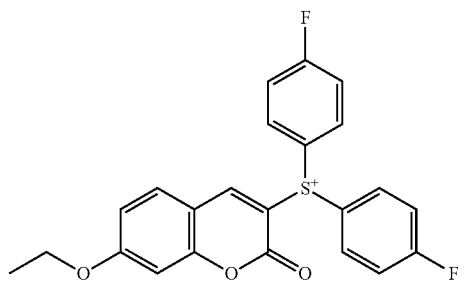
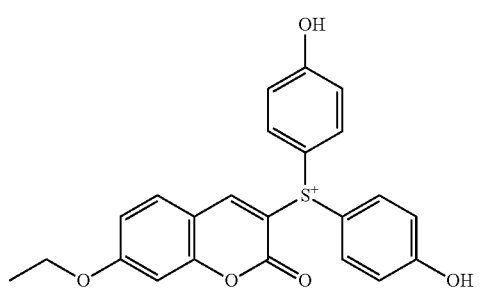
[Chemical Formula 21]
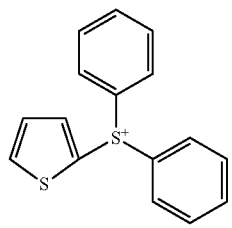
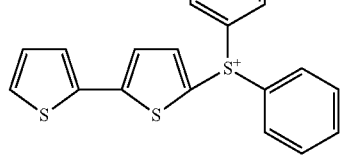

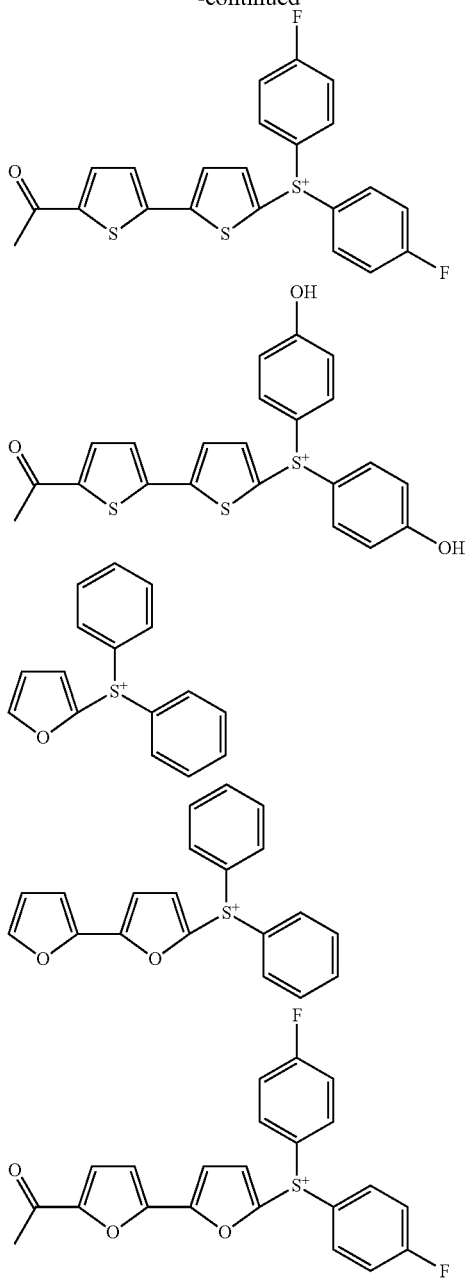

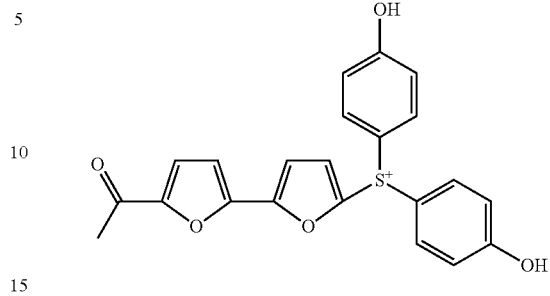

In general formula (9), as $R^{16}$, examples of the alkyl group, the alkoxy group, the alkylcarbonyl group, the arylcarbonyl group, the alkoxycarbonyl group, the aryloxycarbonyl group, the arylthiocarbonyl group, the acyloxy group, the arylthio group, the alkylthio group, the aryl group, the heterocyclic hydrocarbon group, the aryloxy group, the alkylsulfinyl group, the arylsulfinyl group, the alkylsulfonyl group, the arylsulfonyl group, the hydroxy(poly)alkyleneoxy group, the optionally substituted silyl group, the optionally substituted amino group, and the halogen atom are the same as those above-listed for $R^2$ in general formula (1).

In formula (9), $R^{16}$s are independent of one another and therefore may be the same as or different from one another.

In formula (9), $R^{16}$ preferably represents a hydroxy group, an alkoxy group, or a halogen atom, and in particular, preferably represent a hydroxy group, a methoxy group, a 2-hydroxyethoxy group, or a fluorine atom.

In formula (9), $m^{11}$ and $m^{12}$ each represent the number of occurrences of each of $R^{16}$ and $R^{17}$, $m^{11}$ represents an integer of 0 to 5, preferably 0 to 3, more preferably 0 to 2, in particular, preferably 0 or 1; $m^{12}$ represents an integer of 0 to 4, preferably 0 to 3, more preferably 0 to 2, in particular, preferably 0 or 1. When $m^{11}$ and $m^{12}$ are each in the preferred range, the sulfonium salt will have higher photosensitivity.

Preferred specific examples of the group represented by general formula (9) are shown below. In particular, preferred sulfonium cation is the cation having 2-hydroxyethoxy group for $R^{16}$; and having 1 for $m^{11}$

[Chemical Formula 22]

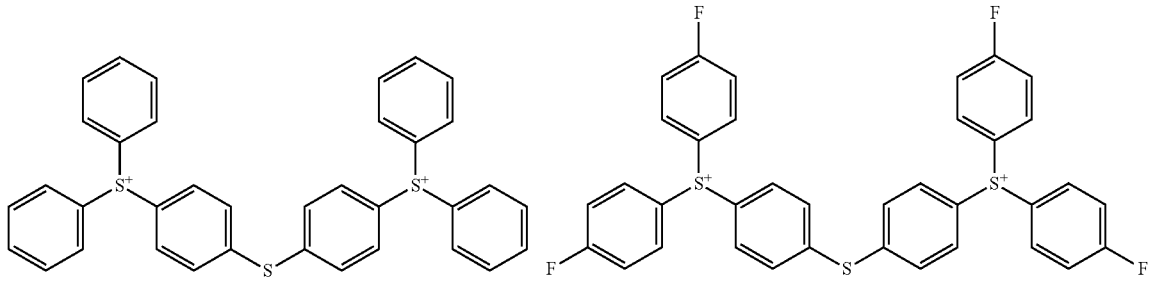

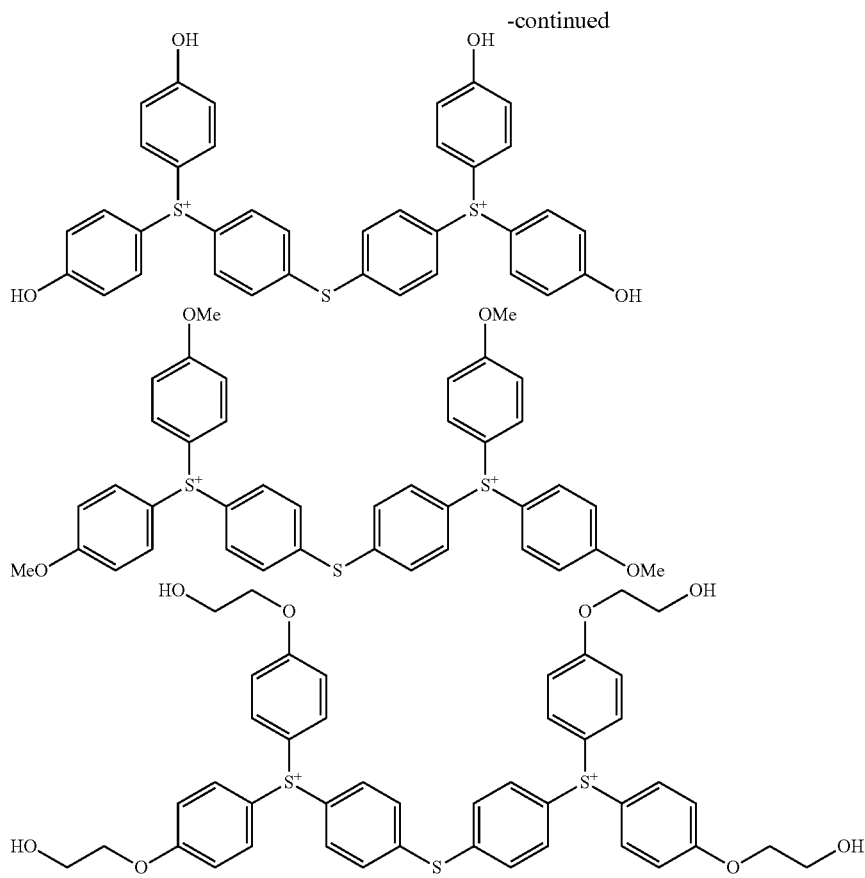

In general formula (10), as $R^{18}$ and $R^{19}$, examples of the alkyl group, the alkoxy group, the alkylcarbonyl group, the arylcarbonyl group, the alkoxycarbonyl group, the aryloxycarbonyl group, the arylthiocarbonyl group, the acyloxy group, the arylthio group, the alkylthio group, the aryl group, the heterocyclic hydrocarbon group, the aryloxy group, the alkylsulfinyl group, the arylsulfinyl group, the alkylsulfonyl group, the arylsulfonyl group, the hydroxy(poly)alkyleneoxy group, the optionally substituted silyl group, the optionally substituted amino group, and the halogen atom are the same as those above-listed for $R^2$ in general formula (1).

In formula (10), $R^{18}$ and $R^{19}$ are independent of one another and therefore may be the same as or different from one another.

In formula (10), $R^{18}$ and $R^{19}$ preferably represent an alkyl group, a hydroxy group, or an alkylcarbonyl group, and in particular, preferably represent a methyl group, a hydroxy group, or an acetyl group.

In formula (10), $m^{13}$ and $m^{14}$ each represent the number of occurrences of each of $R^{18}$ and $R^{19}$, $m^{13}$ represents an integer of 0 to 4, preferably 0 to 3, more preferably 0 to 2, in particular, preferably 0 or 1; $m^{14}$ represents an integer of 0 to 5, preferably 0 to 3, more preferably 0 to 2, in particular, preferably 0 or 1. When $m^{13}$ and $m^{14}$ are each in the preferred range, the sulfonium salt will have higher photosensitivity.

In general formula (10), examples of $R^{20}$ to $R^{23}$ for —$NR^{20}$, $CR^{21}R^{22}$, and —$NCOR^{23}$ of L are the same as those above-listed for —$NR^{12}$, $CR^{13}R^{14}$, and —$NR^{15}$ of Y and Z in general formulas (2) to (8).

Preferred specific examples of the group represented by general formula (10) are shown below. In the formula, - represents a methyl group. In particular, preferred sulfonium cation are the cation having —S— for L, an optionally substituted aryl group for M, and having 3 for n, in formula (10); and the cation having a phenyl group substituted by an acetyl group for M, in formula (10).

[Chemical Formula 23]

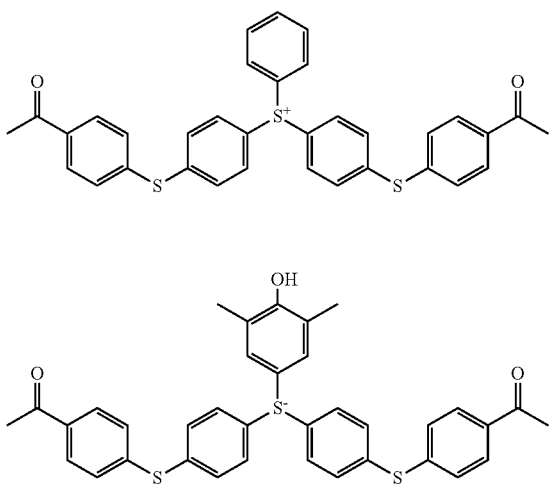

31
-continued
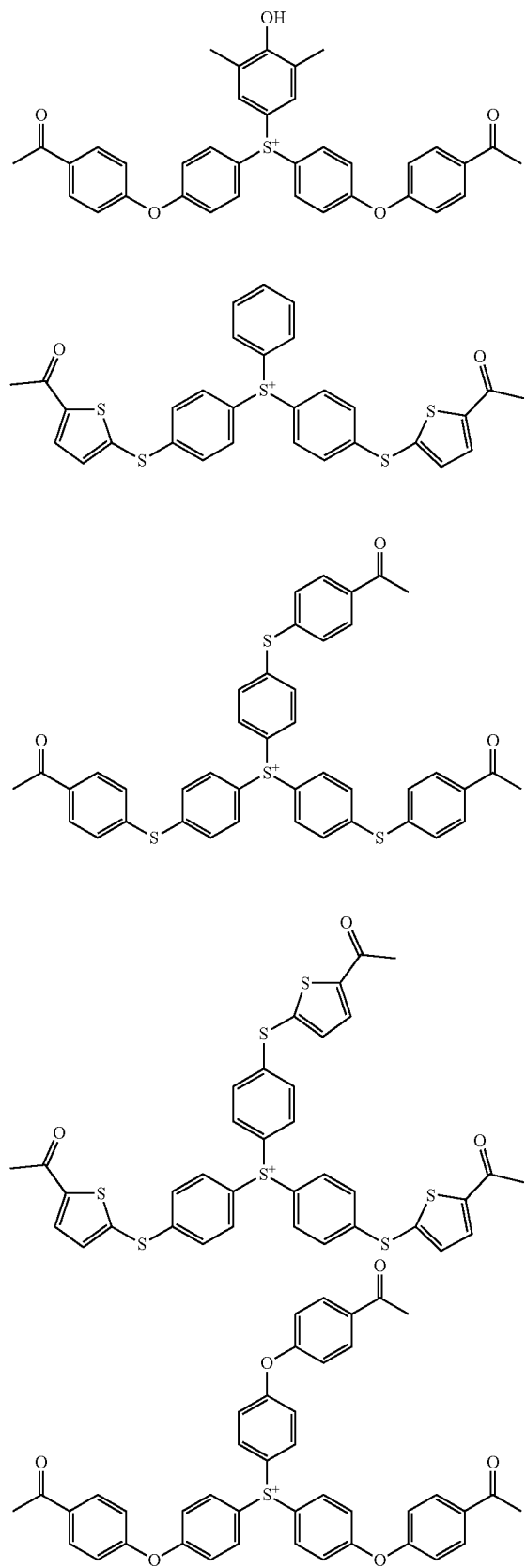
32
-continued
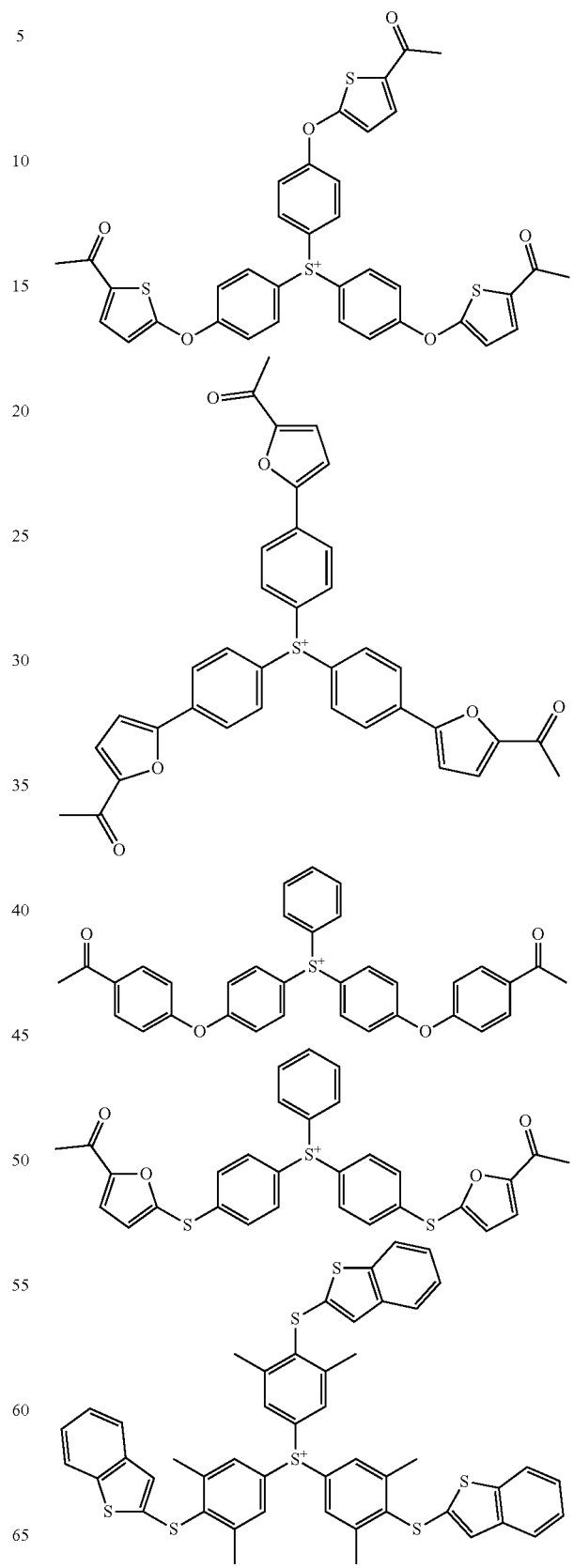

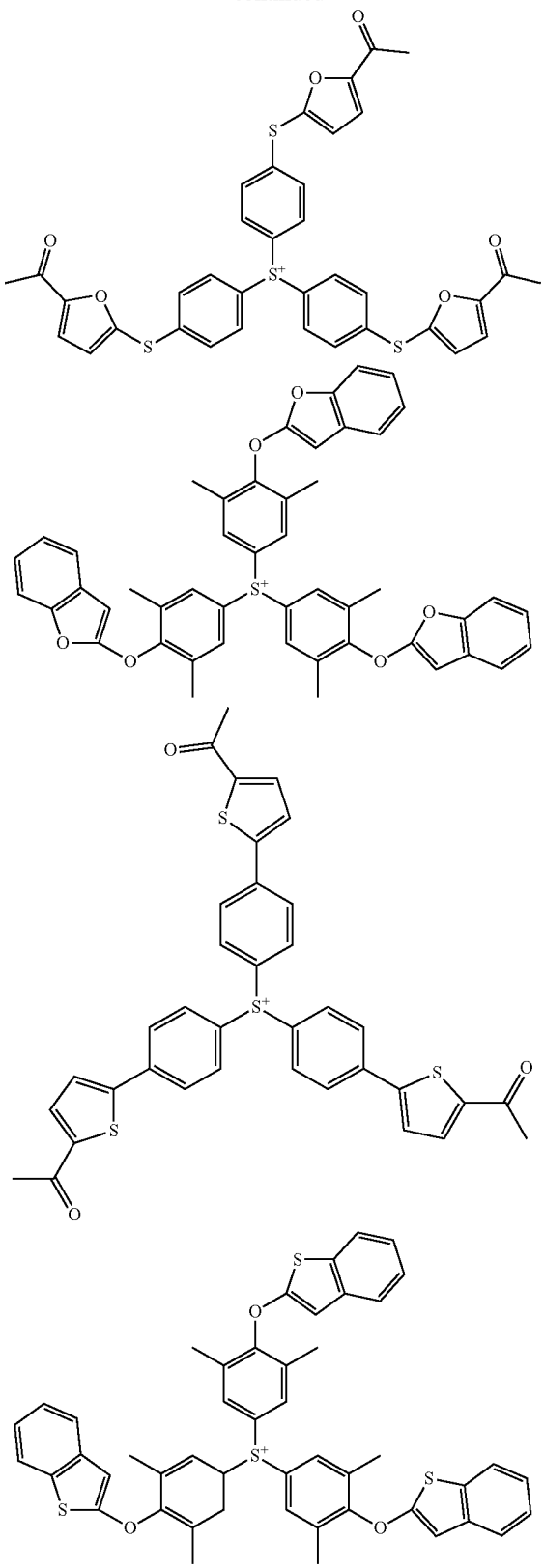

In general formula (11), examples of the aralkyl group for $R^{24}$ and $R^{25}$ include a lower alkyl group substituted by an aryl group having 6 to 10 carbon atoms (such as benzyl, 2-methylbenzyl, 1-naphthylmethyl, and 2-naphthylmethyl).

In general formula (11), as $R^{26}$, examples of the alkoxy group, the alkylcarbonyl group, the arylcarbonyl group, the alkoxycarbonyl group, the aryloxycarbonyl group, the arylthiocarbonyl group, the acyloxy group, the arylthio group, the alkylthio group, the aryl group, the heterocyclic hydrocarbon group, the aryloxy group, the alkylsulfinyl group, the arylsulfinyl group, the alkylsulfonyl group, the arylsulfonyl group, the hydroxy(poly)alkyleneoxy group, the optionally substituted silyl group, the optionally substituted amino group, and the halogen atom are the same as those above-listed for $R^2$ in general formula (1).

In general formula (11), examples of the aryloxy group for $R^{26}$ includes an aryloxy group having 6 to 10 carbon atoms (such as phenoxy, and naphthyloxy).

In general formula (11), examples of the aralkylcarbonyl group for $R^{26}$ include a lower aralkyl group substituted by an aryl group having 6 to 10 carbon atoms (such as benzylcarbonyl, 2-metylbenzylcarbonyl, 1-naphthymethylcarbonyl, and 2-naphthylmethylcarbonyl).

In general formula (11), examples of the aralkyloxycarbonyl group for $R^{26}$ include a lower alkoxycarbonyl group substituted by an aryl group having 6 to 10 carbon atoms (such as benzyloxycarbonyl, 2-methylbenzyloxycarbonyl, 1-naphthylmethyloxycarbonyl, and 2-naphthylmethyloxycarbonyl).

In formula (11), examples of the alkylcarbonyloxy group for $R^{26}$ include straight chain or branched chain alkylcarbonyloxy groups having 2 to 19 carbon atoms (such as acethoxy, ethylcarbonyloxy, propylcarbonyloxy, isopropylcarbonyloxy, butylcarbonyloxy, isobutylcarbonyloxy, sec-butylcarbonyloxy, tert-butylcarbonyloxy, octylcarbonyloxy, and octadecylcarbonyloxy).

In general formula (11), examples of the arylcarbonyloxy group for $R^{26}$ includes an arylcarbonyloxy group having 7 to 11 carbon atoms (such as benzoyloxy, and naphthoyloxy).

In general formula (11), examples of the aralkylcarbonyloxy group for $R^{26}$ include a lower alkylcarbonyl group substituted by an aryl group having 6 to 10 carbon atoms (such as benzylcarbonyloxy, 2-metylbenzylcarbonyloxy, 1-naphthymethylcarbonyloxy, and 2-naphthylmethylcarbonyloxy).

In formula (11), examples of the alkoxycarbonyloxy group for $R^{26}$ include straight chain or branched chain alkoxycarbonyl groups having 2 to 19 carbon atoms (such as methoxycarbonyloxy, ethoxycarbonyloxy, propoxycarbonyloxy, isopropoxycarbonyloxy, buthoxycarbonyloxy, isobuthoxycarbonyloxy, sec-buthoxycarbonyloxy, tert-buthoxycarbonyloxy, octyloxycarbonyloxy, tetradecyloxycarbonyloxy, and octadecyloxycarbonyloxy).

In formula (11), examples of the aryloxycarbonyloxy group for $R^{26}$ include aryloxycarbonyloxy groups having 7 to 11 carbon atoms (such as phenoxycarbonyloxy, and naphthoxycarbonyloxy)

In general formula (11), examples of the aralkyloxycarbonyloxy group for $R^{26}$ include a lower alkoxycarbonyloxy group substituted by an aryl group having 6 to 10 carbon atoms (such as benzyloxycarbonyloxy, 2-metylbenzyloxycarbonyloxy, 1-naphthymethyloxycarbonyloxy, and 2-naphthylmethyloxycarbonyloxy).

In formula (11), $R^{26}$s are independent of one another and therefore may be the same as or different from one another.

In general formula (11), examples of the alkyl group for $R^{24}$ to $R^{26}$ are the same as examples of the alkyl group for $R^2$ in general formula (1).

In formula (11), $R^{26}$ preferably represents a hydroxy group, an alkoxy group, an alkylcarbonyloxy group, or an aralkyloxycarbonyloxy group, and in particular, preferably represents a hydroxy group, a methoxy group, an acethyloxy group, or a benzyloxycarbonyloxy group.

In formula (11), $m^{15}$ represents the number of occurrences of $R^{26}$, $m^{15}$ represents an integer of 0 to 5, preferably 0 to 3, more preferably 0 to 2, in particular, preferably 0 to 1. When $m^{15}$ is in the preferred range, the sulfonium salt will have higher photosensitivity.

Preferred specific examples of the group represented by general formula (11) are shown below. In particular, preferred sulfonium cation are the cation having a methyl group for $R^{24}$, a naphthylbenzyl group for $R^{25}$, a hydroxyl group for $R^{26}$, in formula (11); the cation having a methyl group for $R^{24}$, a benzyl group for $R^{25}$, a hydroxyl group for $R^{26}$, in formula (11); the cation having a methyl group for $R^{24}$, a nitrobenzyl group for $R^{25}$, a hydroxyl group for $R^{26}$, in formula (11); and the cation having a methyl group for $R^{24}$ and $R^{25}$, an acethoxy group for $R^{26}$ in formula (11)

[Chemical Formula 24]

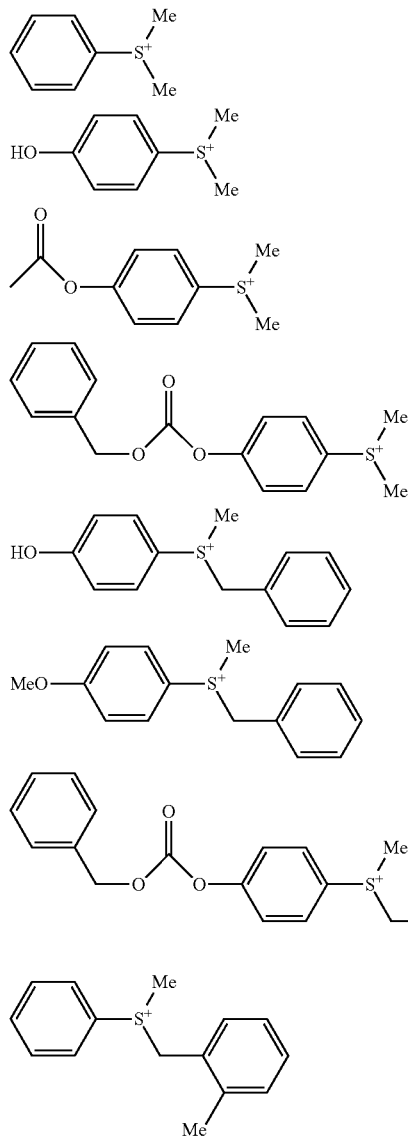

-continued

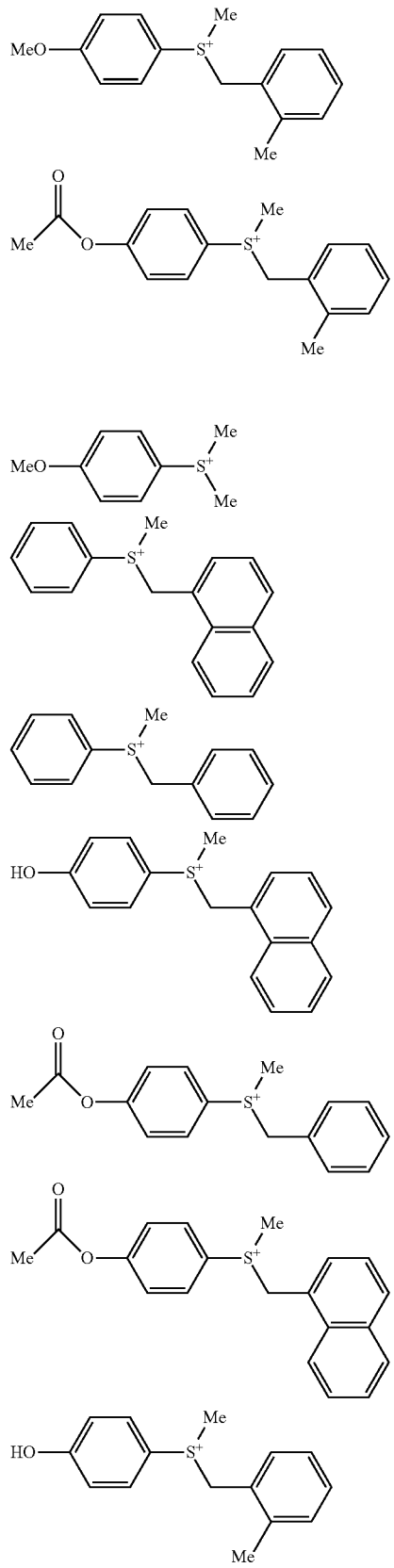

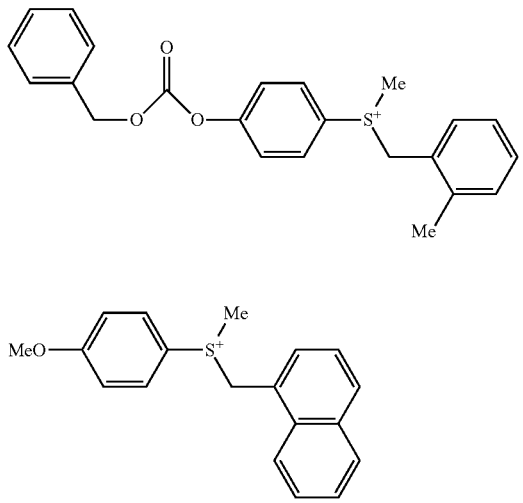

In a gallate anion represented by formula (a), $R^{27}$ to $R^{30}$ each independently represent a phenyl group or a perfluoroalkyl group, and some of hydrogen atoms in these groups may be substituted with a group selected from a perfluoroalkyl group, a perfluoroalkoxy group, a nitro group, a cyano group, an acyl group and a halogen atom.

The perfluoroalkyl group has 1 to 8 carbon atoms, and preferably 1 to 4 carbon atoms. Examples of the perfluoroalkyl group include straight chain perfluoroalkyl group such as trifluoromethyl, pentafluoroethyl, heptafluoropropyl, nonafluorobutyl, perfluoropentyl, perfluorooctyl; branched chain perfluoroalkyl group such as heptafluoro-iso-propyl, nonafluoro-iso-butyl, nonafluoro-sec-butyl, nonafluoro-tert-butyl; in addition, other perfluoroalkyl group such as perfluorocyclopropyl, perfluorocyclobuthyl, perfluorocyclopenthyl, perfluorocyclohexyl.

The perfluoroalkoxy group has 1 to 8 carbon atoms, and preferably 1 to 4 carbon atoms. Examples of the perfluoroalkoxy group include straight chain perfluoroalkoxy group such as trifluoromethoxy, pentafluoroethoxy, heptafluoropropoxy, nonafluorobutoxy, perfluoropentyloxy, perfluorooctyloxy; branched chain perfluoroalkoxy group such as heptafluoro-iso-propoxy, nonafluoro-iso-butoxy, nonafluoro-sec-butoxy, nonafluoro-tert-butoxy.

Examples of the halogen atom include a fluorine atom, a chlorine atom, a bromine atom, and an iodine atom.

Examples of the perfluoroalkyl group are the same as those listed above.

From the viewpoint of cationic polymerization performance, $R^{27}$ to $R^{30}$ are preferably a phenyl group substituted with at least one selected from the group of a perfluoroalkyl group and a fluorine atom.

Preferable examples of $R^{27}$ to $R^{30}$ include pentafluorophenyl group ($C_6F_5$), trifluorophenyl group ($C_6H_2F_3$), tetrafluorophenyl group ($C_6HF_4$), trifluoromethylphenyl group ($CF_3C_6H_4$), bis(trifluoromethyl)phenyl group (($CF_3)_2C_6H_3$), pentafluoroethylphenyl group ($CF_3CF_2C_6H_4$), bis(pentafluoroethyl)phenyl group (($CF_3CF_2)_2C_6H_3$), fluoro-trifluoromethylphenyl group ($CF_3C_6H_3F$), fluoro-bis(trifluoromethyl)phenyl group (($CF_3)_2C_6H_2F$), fluoro-pentafluoroethylphenyl group ($CF_3CF_2C_6H_3F$), fluoro-bis(pentafluoroethyl)phenyl group (($CF_3CF_2)_2C_6H_2F$), pentachlorophenyl group ($C_6CL_5$), trichlorophenyl group ($C_6H_2CL_3$), tetrachlorophenyl group ($C_6HCL_4$), trichloromethylphenyl group ($CCL_3C_6H_4$), bis(trichloromethyl)phenyl group (($CCL_3)_2C_6H_3$), pentachloroethylphenyl group ($CCL_3CCL_2C_6H_4$), bis(pentachloroethyl)phenyl group (($CCL_3CCL_2)_2C_6H_3$), cloro-trichloromethylphenyl group ($CCL_3C_6H_3CL$), cloro-bis(trichloromethyl)phenyl group (($CCL_3)_2C_6H_2CL$), cloro-pentaclhoroethylphenyl group ($CCL_3CCL_2C_6H_3CL$), cloro-bis(pentachloroethylphenyl group (($CCL_3CCL_2)_2C_6H_2CL$), nitrophenyl group ($C_6H_4NO_2$), cyano phenyl group ($NCC_6H_4$), acylphenyl group ($CH_3COC_6H_4$)

Among them, more preferred are pentafluorophenyl group ($C_6F_5$), and bis(trifluoromethyl)phenyl group (($CF_3)_3C_6H_3$), and in particular, preferred is pentafluorophenyl group ($C_6F_5$).

Specific examples of the gallate anion represented by formula (a) are shown below. In particular, preferred are the gallate anions represented by $[Ga(C_6F_5)_4]^-$ or $[Ga((CF_3)_2C_6H_3)_4]^-$.

[Chemical Formula 25]

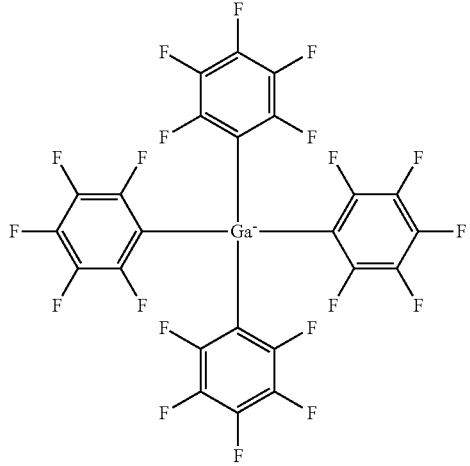

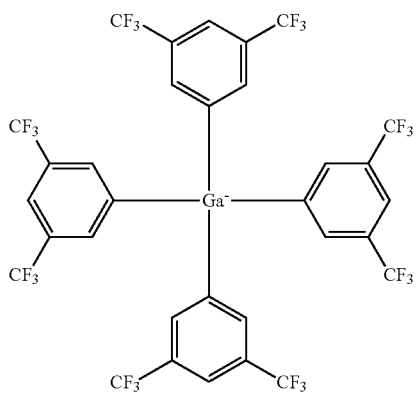

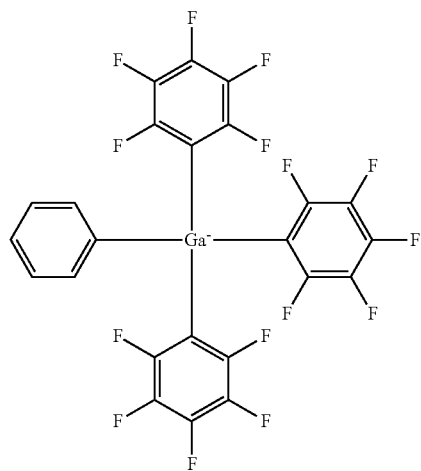
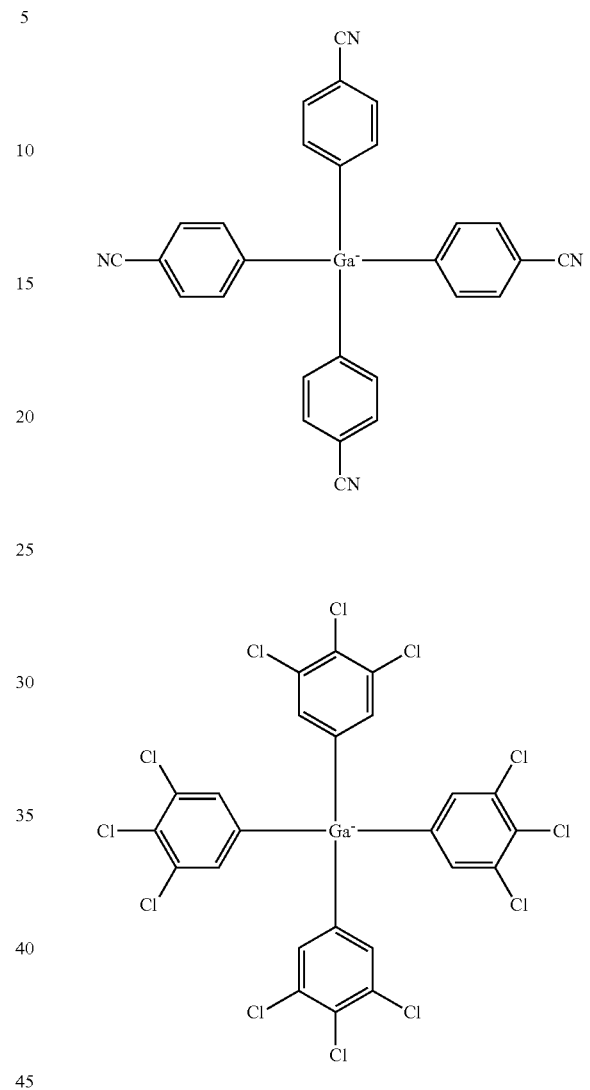
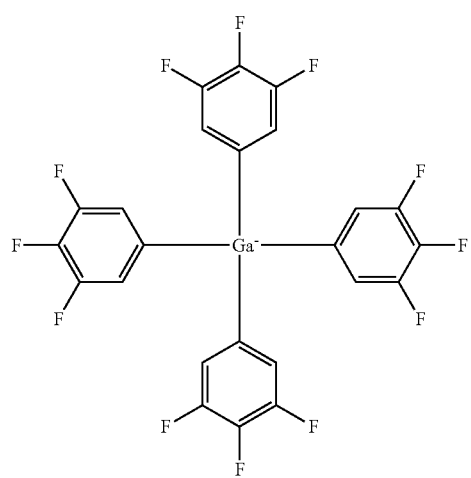
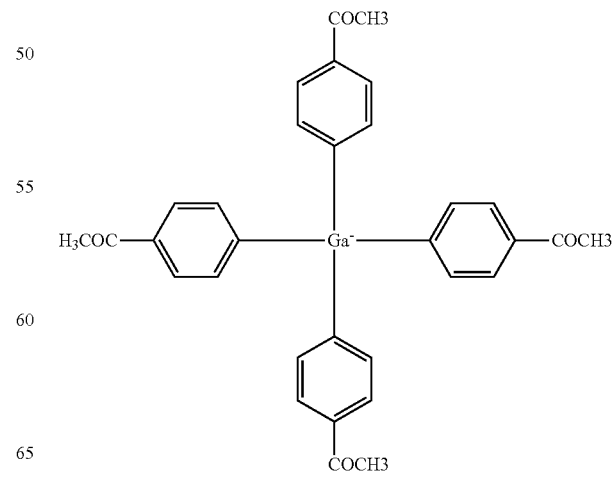

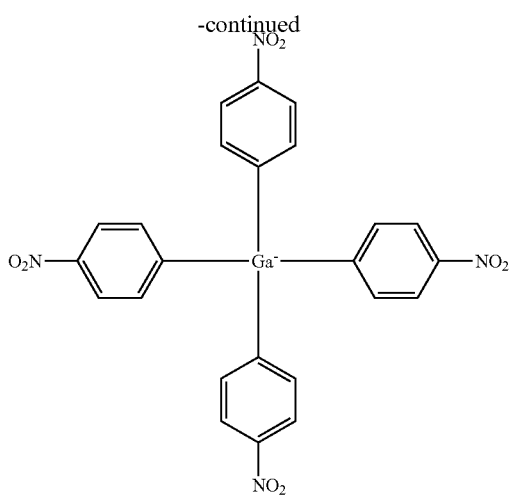

For ensuring that the sulfonium salt (acid generator) is easily dissolved in a cationic polymerizable compound, the sulfonium salt may be previously dissolved in a solvent which does not hinder polymerization or crosslinking reaction.

Examples of the solvent include carbonates such as propylene carbonate, ethylene carbonate, 1,2-butylene carbonate, dimethyl carbonate, and diethyl carbonate; ketones such as acetone, methyl ethyl ketone, cyclohexanone, methyl isoamyl ketone, and 2-heptanone; polyhydric alcohols and derivatives thereof, such as ethylene glycol, ethylene glycol monoacetate, diethylene glycol, diethylene glycol monoacetate, propylene glycol, propylene glycol monoacetate, dipropylene glycol, and monomethyl ether, monoethyl ether, monopropyl ether, monobutyl ether, or monophenyl ether of dipropylene glycol monoacetate; cyclic ethers such as dioxane; esters such as ethyl formate, methyl lactate, ethyl lactate, methyl acetate, ethyl acetate, butyl acetate, methyl pyruvate, methyl acetoacetate, ethyl acetoacetate, ethyl pyruvate, ethyl ethoxyacetate, methyl methoxypropionate, ethyl ethoxypropionate, methyl 2-hydroxypropionate, ethyl 2-hydroxypropionate, ethyl 2-hydroxy-2-methylpropionate, methyl 2-hydroxy-3-methylbutanoate, 3-methoxybutyl acetate, and 3-methyl-3-methoxybutyl acetate; and aromatic hydrocarbons such as toluene and xylene.

When a solvent is used, the amount of the solvent used is preferably from 15 to 1000 parts by weight, more preferably from 30 to 500 parts by weight, based on 100 parts by weight of the sulfonium salt (acid generator) in the present invention. A single solvent may be used alone or two or more solvents may be used in combination.

The heat- or energy ray-curable composition in the present invention (hereinafter, in some cases, referred to as a curable composition) contains the above-mentioned acid generator and a cationic polymerizable compound.

Examples of the cationic polymerizable compound as a constituent component of the curable composition include cyclic ethers (such as epoxide and oxetane), ethylenically unsaturated compounds (such as vinyl ether and styrene species), bicycloorthoesters, spiroorthocarbonates, and spiroorthoesters Known epoxides and the like may be used as epoxides, examples of which include aromatic epoxides, alicyclic epoxides, and aliphatic epoxides.

Examples of the aromatic epoxides include glycidyl ethers of monohydric or polyhydric phenols having at least one aromatic ring (such as phenol, bisphenol A, phenol novolac, and alkylene oxide adducts thereof).

Examples of the alicyclic epoxides include compounds obtained by epoxidation of compounds having at least one cyclohexene or cyclopentene ring with an oxidizing agent (such as 3,4-epoxycyclohexylmethyl-3,4-epoxycyclohexanecarboxylate).

Examples of the aliphatic epoxides include polyglycidyl ethers of aliphatic polyhydric alcohols or alkylene oxide adducts thereof (such as 1,4-butanediol diglycidyl ether and 1,6-hexanediol diglycidyl ether), polyglycidyl esters of aliphatic polybasic acids (such as diglycidyl tetrahydrophthalate), and epoxidized long-chain unsaturated compounds (such as epoxidized soybean oil and epoxidized polybutadiene).

Known oxetanes and the like may be used as oxetanes, examples of which include 3-ethyl-3-hydroxymethyloxetane, 2-ethylhexyl(3-ethyl-3-oxetanylmethyl)ether, 2-hydroxyethyl(3-ethyl-3-oxetanylmethyl)ether, 2-hydroxypropyl(3-ethyl-3-oxetanylmethyl)ether, 1,4-bis[(3-ethyl-3-oxetanylmethoxy)methyl]benzene, oxetanylsilsesquioxetane, and phenol novolac oxetane.

Known cationic polymerizable monomers and the like may be used as ethylenically unsaturated compounds, examples of which include aliphatic monovinyl ethers, aromatic monovinyl ethers, polyfunctional vinyl ethers, styrenes, and cationic polymerizable nitrogen-containing monomers.

Examples of the aliphatic monovinyl ethers include methyl vinyl ether, ethyl vinyl ether, butyl vinyl ether, and cyclohexyl vinyl ether.

Examples of the aromatic monovinyl ethers include 2-phenoxyethyl vinyl ether, phenyl vinyl ether, and p-methoxyphenyl vinyl ether.

Examples of the polyfunctional vinyl ethers include butanediol-1,4-divinyl ether and triethylene glycol divinyl ether.

Examples of the styrene species include styrene, α-methylstyrene, p-methoxystyrene, and p-tert-butoxystyrene.

Examples of the cationic polymerizable nitrogen-containing monomers include N-vinylcarbazole and N-vinylpyrrolidone.

Examples of the bicycloorthoesters include 1-phenyl-4-ethyl-2,6,7-trioxabicyclo[2.2.2]octane and 1-ethyl-4-hydroxymethyl-2,6,7-trioxabicyclo[2.2.2]octane.

Examples of the spiroorthocarbonates include 1,5,7,11-tetraoxaspiro[5.5]undecane and 3,9-dibenzyl-1,5,7,11-tetraoxaspiro[5.5]undecane.

Examples of the spiroorthoesters include 1,4,6-trioxaspiro[4.4]nonane, 2-methyl-1,4,6-trioxaspiro[4.4]nonane, and 1,4,6-trioxaspiro[4.5]decane.

Further, a polyorganosiloxane having at least one cationic polymerizable group in one molecule can be used (those described in JP-A No. 2001-348482, JP-A No. 2000-281965, JP-A No. 7-242828, JP-A No. 2008-195931, Journal of Polym. Sci., Part A, Polym. Chem., Vol. 28, 497 (1990) and so on).

These polyorganosiloxanes may be any one of straight chain, branched chain and cyclic polyorganosiloxanes, or a mixture thereof.

Among these cationic polymerizable compounds, epoxides, oxetanes, and vinyl ethers are preferred, epoxides and oxetane are more preferred, and alicyclic epoxides and oxetanes are particularly preferred. These cationic polymerizable compounds may be used alone or in combination of two or more.

The content of the sulfonium salt formed of a sulfonium cation (acid generator) of the present invention in a curable composition is preferably from 0.05 to 20 parts by weight, more preferably from 0.1 to 10 parts by weight, based on 100 parts by weight of the cationic polymerizable compound. Within the range, the cationic polymerizable compound can be more sufficiently polymerized, so that the physical properties of the cured product can be further improved. It will be understood that the content may be determined taking into account various factors such as the properties of the cationic polymerizable compound, the type and irradiation dose of the active energy ray, the temperature, the curing time, the humidity, and the thickness of the coating film, and is not limited to the above range.

If necessary, the curable composition of the present invention may contain known additives (such as a sensitizer, a pigment, a filler, an electroconductive particle, an antistatic agent, a flame retardant, an anti-foaming agent, a fluidity controlling agent, a light stabilizer, an antioxidant, a tackifier, an ion scavenger, an anti-coloring agent, a solvent, a nonreactive resin, and a radically-polymerizable compound).

Basically, a sensitizer does not need to be contained in the curable composition of the present invention, but a sensitizer as an agent that complements the curability can be contained therein, as necessary. As such a sensitizer, a known (JP-A-11-279212, JP-A-09-183960, or the like) sensitizer and the like can be used, and examples thereof include anthracenes {anthracene, 9,10-dibutoxyanthracene, 9,10-dimethoxyanthracene, 2-ethyl-9,10-dimethoxyanthracene, 2-tert-buthyl-9,10-dimethoxyanthracene, 2,3-dimethyl-9,10-dimethoxyanthracene, 9-methoxy-10-methylanthracene, 9,10-diethoxyanthracene, 2-ethyl-9,10-dimethoxyanthracene, 2-tert-buthyl-9,10-diethoxyanthracene, 2,3-dimethyl-9,10-diethoxyanthracene, 9-ethoxy-10-methylanthracene, 9,10-dipropoxyanthracene, 9,10-diisopropoxyanthracene, 9,10-diethoxyanthracene, 2-ethyl-9,10-dipropoxyanthracene, 2-tert-buthyl-9,10-dipropoxyanthracene, 2,3-dimethyl-9,10-dipropoxyanthracene, 9-isopropoxy-10-methylanthracene, 9,10-dibenzyloxyanthracene, 2-ethyl-9,10-dibenzyloxyanthracene, 2-tert-buthyl-9,10-dibenzyloxyanthracene, 2,3-dimethyl-9,10-dibenzyloxyanthracene, 9-benzyloxy-10-methylanthracene, 9,10-di-α-methylbenzyloxyanthracene, 2-ethyl-9,10-di-α-methylbenzyloxyanthracene, 2-tert-buthyl-9,10-di-α-methylbenzyloxyanthracene, 2,3-dimethyl-9,10-di-α-methylbenzyloxyanthracene, 9-(α-methylbenzyloxy)-10-methylanthracene, 9,10-diphenylanthracene, 9-methoxyanthracene, 9-ethoxyanthracene, 9-methylanthracene, 9-bromoanthracene, 9-methlthioanthracene, 9-ethlthioanthracene and the like}; pyrene; 1,2-benzanthracene; perylene; tetracene; coronene; thioxanthones {thioxanthone, 2-methylthioxanthone, 2-ethylthioxanthone, 2-chlorothioxanthone, 2-isopropylthioxanthone, 2,4-diethylthioxanthone, and the like}; phenothiazine and derivatives thereof {phenothiazine, N-methylphenothiazine, N-ethylphenothiazine, N-phenylphenothiazine, and the like}; xanthone; naphthalenes {1-naphthol, 2-naphthol, 1-methoxynaphthalene, 2-methoxynaphthalene, 1,4-dihydroxynaphthalene, 1,5-dihydroxynaphthalene, 1,6-dihydroxynaphthalene, 2,7-dihydroxynaphthalene, 2,7-dimethoxynaphthalene, 1,1'-thiobis(2-naphthol), 1,1'-bi(2-naphthol), 4-methoxy-1-naphthol, and the like}; ketones {dimethoxyacetophenone, diethoxyacetophenone, 2-hydroxy-2-methyl-1-phenylpropane-1-one, 4'-isopropyl-2-hydroxy-2-methylpropiophenone, 2-hydroxymethyl-2-methylpropiophenone, 2,2-dimethoxy-1,2-diphenylethane-1-on, p-dimethylaminoacetophenone, p-tert-buthyldichloroacetophenone, p-tert-buthyltrichloroacetophenone, p-azidebenzalacetophenone, 1-hydroxycyclohexylphenylketone, benzoin, benzoinmethylether, benzoinethylether, benzoinisopropylether, benzoin-n-buthylether, benzoin-iso-buthylether, 1-[4-(2-hydroxyethoxy)phenyl]-2-hydroxy-2-methyl-1-propane-1-on, benzophenone, methyl o-benzoilbenzoate, michler's ketone, 4,4'-bisdiethylaminobenzophenone, 4,4'-dichlorobenzophenone, 4-benzoyl-4'-methyldiphenyl sulfide, and the like}; carbazoles {N-phenylcarbazole, N-ethylcarbazole, poly-N-vinylcarbazole, N-glycidylcarbazole, and the like}; chrysenes {1,4-dimethoxychrysene, 1,4-diethoxychrysene, 1,4-dipropoxychrysene, 1,4-dibenzyloxychrysene, 1,4-di-α-methylbenzyloxychrysene, and the like}; phenanthrenes {9-hydroxyphenanthrene, 9-methoxyphenanthrene, 9-ethoxyphenanthrene, 9-benzyloxyphenanthrene, 9,10-dimethoxyphenanthrene, 9,10-diethoxyphenanthrene, 9,10-dipropoxyphenanthrene, 9,10-dibenzyloxyphenanthrene, 9,10-di-α-methylbenzyloxyphenanthrene, 9-hydroxy-10-methoxyphenanthrene, 9-hydroxy-10-ethoxyphenanthrene, and the like}, and the like.

When a sensitizer is contained, the content of the sensitizer is preferably from 1 to 300 parts by weight, more preferably from 5 to 200 parts by weight, based on 100 parts of the acid generator.

Known pigments and the like may be used as pigments, examples of which include inorganic pigments (such as titanium oxide, iron oxide, and carbon black) and organic pigments (such as azo pigments, cyanine pigments, phthalocyanine pigments, and quinacridone pigments).

When a pigment is contained, the content of the pigment is preferably from 0.5 to 400,000 parts by weight, more preferably from 10 to 150,000 parts by weight, based on 100 parts of the acid generator.

Known fillers and the like may be used as fillers, examples of which include fused silica, crystalline silica, calcium carbonate, aluminum oxide, aluminum hydroxide, zirconium oxide, magnesium carbonate, mica, talc, calcium silicate, lithium aluminum silicate, and the like.

When a filler is contained, the content of the filler is preferably from 50 to 600,000 parts by weight, more preferably 300 to 200,000 parts by weight, based on 100 parts of the acid generator.

Known electroconductive particles can be used as electroconductive particles, and metal particles of Ni, Ag, Au, Cu, Pd, Pb, Sn, Fe, Ni, Al and the like, and plated metal particles obtained by further plating the above-mentioned metal particles with a metal, plated resin particles obtained by plating resin particles with a metal, particles of a substance having conductivity such as carbon, or the like can be used.

When electroconductive particles are contained, the content of the electroconductive particles is preferably from 50 to 30000 parts by weight, more preferably from 100 to 20000 parts by weight, based on 100 parts of the acid generator.

Known antistatic agents and the like may be used as antistatic agents, examples of which include nonionic antistatic agents, anionic antistatic agents, cationic antistatic agents, ampholytic antistatic agents, and high molecular weight antistatic agents.

When an antistatic agent is contained, the content of the antistatic agent is preferably from 0.1 to 20,000 parts by weight, more preferably from 0.6 to 5,000 parts by weight, based on 100 parts of the acid generator.

Known flame retardants and the like may be used as flame retardants, examples of which include inorganic flame retardants {such as antimony trioxide, antimony pentoxide, tin oxide, tin hydroxide, molybdenum oxide, zinc borate, barium metaborate, red phosphorus, aluminum hydroxide, magnesium hydroxide, and calcium aluminate}; bromine flame retardants {such as tetrabromophthalic anhydride, hexabromobenzene, and decabromobiphenyl ether}; and phosphate flame retardants {such as tris(tribromophenyl) phosphate}.

When a flame retardant is contained, the content of the flame retardant is preferably from 0.5 to 40,000 parts by weight, more preferably from 5 to 10,000 parts by weight, based on 100 parts of the acid generator.

Known anti-foaming agents and the like may be used as anti-foaming agents, examples of which include alcoholic anti-foaming agents, metallic soap anti-foaming agents, phosphate anti-foaming agents, fatty acid ester anti-foaming agents, polyether anti-foaming agents, silicone anti-foaming agents, and mineral oil anti-foaming agents.

Known fluidity controlling agents and the like may be used as fluidity controlling agents, examples of which include hydrogenated castor oil, oxidized polyethylene, organic bentonite, colloidal silica, amide wax, metallic soap, and acrylic ester polymers.

Known light stabilizers and the like may be used as light stabilizers, examples of which include ultraviolet absorbing stabilizers {such as benzotriazole, benzophenone, salicylates, cyanoacrylates, and derivatives thereof}; radical scavenging stabilizers {such as hindered amines}; and quenching stabilizers {such as nickel complexes}.

Known antioxidants and the like may be used as antioxidants, examples of which include phenolic antioxidants (such as monophenolic, bisphenolic, and macromolecular phenolic antioxidants), sulfur-based antioxidants, and phosphorus-based antioxidants.

Known tackifiers and the like may be used as tackifiers, examples of which include coupling agents, silane coupling agents, and titanium coupling agents.

Known ion scavenger and the like may be used as ion scavenger, examples of which include organoaluminum (such as alkoxyaluminum and phenoxyaluminum).

Known anti-coloring agents and the like may be used as anti-coloring agents, and antioxidants are generally effective, examples of which include phenolic antioxidants (such as monophenolic, bisphenolic, and macromolecular phenolic antioxidants), sulfur-based antioxidants, and phosphorus-based antioxidants.

When an anti-foaming agent, a fluidity controlling agent, a light stabilizer, an antioxidant, a tackifier, an ion scavenger, or an anti-coloring agent is contained, the content of each material is preferably from 0.1 to 20,000 parts by weight, more preferably from 0.5 to 5,000 parts by weight, based on 100 parts of the acid generator.

Any solvent that can be used to dissolve the cationic polymerizable compound or to control the viscosity of the energy ray-curable composition may be used as solvents, examples of which include those listed for the above acid generator.

When a solvent is contained, the content of the solvent is preferably from 50 to 2,000,000 parts by weight, more preferably from 200 to 500,000 parts by weight, based on 100 parts of the acid generator.

Examples of the nonreactive resin include polyester, polyvinyl acetate, polyvinyl chloride, polybutadiene, polycarbonate, polystyrene, polyvinyl ether, polyvinyl butyral, polybutene, hydrogenated styrene-butadiene block copolymers, copolymers of (meth)acrylic acid esters, and polyurethane. The number average molecular weight of these resins is preferably from 1,000 to 500,000, more preferably from 5,000 to 100,000 (the number average molecular weight is a value measured by a general method such as GPC).

When a nonreactive resin is contained, the content of the nonreactive resin is preferably from 5 to 400,000 parts by weight, more preferably from 50 to 150,000 parts by weight, based on 100 parts of the acid generator.

When a nonreactive resin is contained, it is preferably dissolved in advance in a solvent so that it can be easily dissolved in the cationic polymerizable compound or the like.

Known radically-polymerizable compounds and the like may be used as radically-polymerizable compounds {such as those described in "Photopolymer Handbook" edited by The Technical Association of Photopolymers, Japan (1989, Kogyo Chosakai Publishing, Co., Ltd.), "UV/EB Koka Gijutsu" (Technology of UV/EB Curing), edited by Sogo Gijutsu Center (1982, Sogo Gijutsu Center), "UV/EB Koka Zairyo" (UV/EB Curable Materials), edited by RadTech Japan (1992, CMC), and "UV-Koka niokeru Koka-Furyo/Sogai-Genin to Sonotaisaku" (Causes of UV Curing Defects/Inhibition and Remedies Therefor), edited by TECHNICAL INFORMATION INSTITUTE (2003, TECHNICAL INFORMATION INSTITUTE CO., LTD.)}, examples of which include monofunctional monomers, bifunctional monomers, polyfunctional monomers, epoxy (meth)acrylate, polyester (meth)acrylate, and urethane (meth)acrylate.

When a radically-polymerizable compound is contained, the content of the radically-polymerizable compound is preferably from 5 to 400,000 parts by weight, more preferably from 50 to 150,000 parts by weight, based on 100 parts of the acid generator.

When a radically-polymerizable compound is contained, a radical polymerization initiator initiating polymerization with heat or light is preferably used so that the compound can be polymerized by radical polymerization.

Known radical polymerization initiators and the like may be used as radical polymerization initiators, examples of which include thermal radical polymerization initiators (such as organic peroxides and azo compounds) and photoradical polymerization initiators (such as acetophenone-based initiators, benzophenone-based initiators, Michler's ketone-based initiators, benzoin-based initiators, thioxanthone-based initiators, and acylphosphine-based initiators.

When a radical polymerization initiator is contained, the content of the radical polymerization initiator is preferably from 0.01 to 20 parts by weight, more preferably from 0.1 to 10 parts by weight, based on 100 parts of the radically-polymerizable compound.

The curable composition of the present invention may be prepared by uniformly mixing and dissolving the cationic polymerizable compound, the acid generator, and if necessary an optional additive (s) at room temperature (about 20 to 30° C.) or if necessary, under heating (about 40 to 90° C.), or by further kneading them with a triple-roll mill or the like.

The curable composition of the present invention may be cured by irradiation with heat or energy rays so that a cured product can be obtained.

The energy ray may be of any energy ray as long as it has an energy to induce the decomposition of the acid generator of the present invention, preferred examples of which include energy rays in the ultraviolet to visible light region (wavelength: from about 100 to about 800 nm) obtained from a low pressure-, medium pressure-, high pressure-, or ultra high pressure-mercury lamp, a metal halide lamp, an LED lamp, a xenon lamp, a carbon arc lamp, a fluorescent lamp, a semiconductor solid-state laser, an argon laser, a He—Cd laser, a KrF excimer laser, an ArF excimer laser, or an $F_2$ laser. Radiations with a high energy, such as electron beams or X-rays may also be used as the energy rays.

While the energy ray irradiation time is influenced by the intensity of the energy rays or the permeability of the energy rays to the energy ray-curable composition, an energy ray exposure time of about 0.1 to 10 seconds is enough at room temperature (about 20 to 30° C.). However, if the permeability of the energy rays is low or if the thickness of the energy ray-curable composition is large, for example, it is sometimes preferred to spend more time. Most energy ray-curable compositions are cured by cationic polymerization in 0.1 seconds to several minutes after the irradiation with energy rays. If necessary, however, post-curing may be performed by heating at a temperature of room temperature (about 20 to 30° C.) to 250° C. for several seconds to several hours after the irradiation with energy rays.

As a heating method by which a curable composition is cured, conventionally known methods such as a heat circulation type heating method, an infrared heating method, and a high frequency heating method can be used.

The heating temperature required for curing is not particularly limited as long as the heating temperature lies within a range where curing proceeds sufficiently and a base material is not degraded, and lies within the range of preferably 50° C. to 250° C. and more preferably 80° C. to 200° C., and the heating time varies with the heating temperature, but the heating time is preferably several minutes to several hours from an aspect of productivity.

Here, the base material is a material to be coated or filled with the curable composition of the present invention, and a known material can be appropriately used. Examples of the base material in the present invention include resin films such as PET films, polypropylene films and polyimide films, metal foils such as aluminum foils, substrates of glass, copper, aluminum and the like, devices, light emitting diode elements, transistors and integrated circuits, and also include elements or circuits formed on the substrates described above.

The acid generator of the present invention, which can generate a strong acid upon irradiation with heat or light, may also be used as a acid generator for known chemically amplified resist materials (such as those described in JP-A No. 2003-267968, JP-A No. 2003-261529, and JP-A No. 2002-193925)

Examples of the chemically amplified resist materials include (1) a two-component chemically amplified positive resist comprising, as essential ingredients, a photoacid generator and a resin that can be made soluble in an alkali developing solution by the action of an acid; (2) a three-component chemically amplified positive resist comprising, as essential ingredients, a resin soluble in an alkali developing solution, a dissolution inhibitor that can be made soluble in an alkali developing solution by the action of an acid, and a photoacid generator; and (3) a chemically amplified negative resist comprising, as essential ingredients, a resin soluble in an alkali developing solution, a crosslinking agent that can crosslink the resin to make the resin insoluble in an alkali developing solution when heated in the presence of an acid, and a photoacid generator.

EXAMPLES

Hereinafter, the present invention will be further described by reference to examples, but the present invention is not intended to be limited thereto. It should be noted that a part means a part by weight and % means % by weight unless otherwise stated.

(Production Example 1) Synthesis of a lithium tetrakis(pentafluorophenyl)gallate Charged were 360 parts of ultra-dehydrated diethyl ether and 30 parts of pentafluorobromobenzene in a 125 mL four-necked flask thoroughly dried under a nitrogen atmosphere, and the mixture was cooled to −78° C. using a dry ice/acetone bath. Added dropwise was 70 parts of a 2.5 mol/L n-butyllithium hexane solution over 10 minutes, and the mixture was then stirred at −78° C. for 30 minutes. Thereto was added dropwise 68 parts of a diethyl ether solution dissolved of 5 parts gallium (III) chloride over 10 minutes, and the mixture was stirred at −78° C. for 3 hours. The reaction liquid was stirred while being gradually returned to room temperature, and the reaction liquid was further stirred for 5 hours after being returned to room temperature. The precipitated solid was filtered, the reaction liquid was transferred to an evaporator, and the solvent was distilled off to obtain an off-white product. The product was washed with 50 parts of ultra-dehydrated hexane three times, and dried in vacuum overnight to obtain lithium tetrakis (pentafluorophenyl)gallate. The product was identified by $^{19}$F-NMR.

(Production Example 13) Synthesis of a lithium tetrakis(3,5-bis(trifluoromethyl)phenyl)gallate A lithium tetrakis(3,5-bis(trifluoromethyl)phenyl)gallate was obtained as in Production Example 1, except that 30 parts of pentafluorobromobenzene was replaced with 35.6 parts of 1-bromo-3,5 bis(trifluoromethyl)benzene. The product was identified by $^{19}$F-NMR.

[Example 1] Synthesis of Photoacid Generator (A-1)

Charged were 0.95 parts of 2-isopropylthioxanthone, 0.8 parts of biphenyl, 7.4 parts of acetic acid, 2.3 parts of dichloromethane, and 7.6 parts of acetic anhydride in a reactor. Thereto was added dropwise 4.8 parts of concentrated sulfuric acid while maintaining the temperature at 15° C. or less and the reaction solution was stirred for 2 hours. The reaction solution was allowed to rise to room temperature and poured into 100 parts of ion-exchanged water. The mixture was extracted with 100 parts of dichloromethane, and the dichloromethane layer was washed with ion-exchanged water until the pH of the water layer became neutral. Into the dichloromethane layer, was added 3.26 parts of lithium tetrakis(pentafluorophenyl)gallate, and stirred for 1 hour. The dichloromethane layer was washed with ion-exchanged water three times by liquid-liquid separation, and then the dichloromethane layer was transferred to a rotary evaporator, and the solvent was removed by distillation, so that A-1 was obtained. The product was identified by $^1$H-NMR.

[Chemical Formula 26]

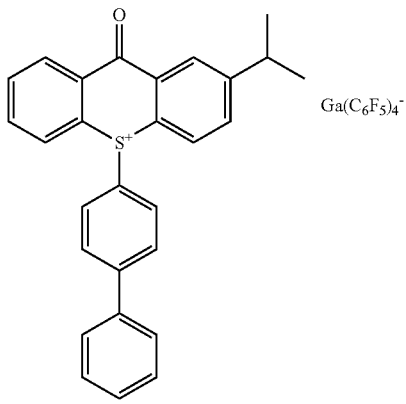

A-1

[Example 2] Synthesis of Photoacid Generator (A-2)

(A-2) was obtained as in Example 1, except that 3.26 parts of lithium tetrakis(pentafluorophenyl)gallate was replaced with 3.95 parts of lithium tetrakis(3,5-bis(trifluoromethyl)phenyl)gallate. The product was identified by $^1$H-NMR.

[Chemical Formula 27]

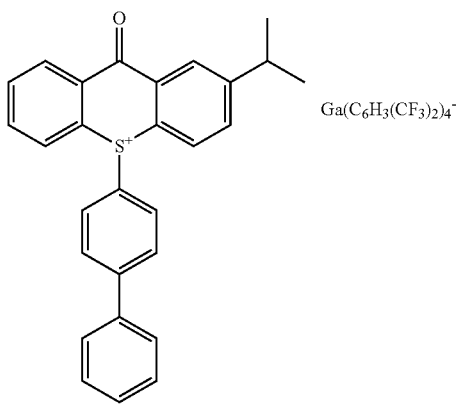

A-2

[Example 3] Synthesis of Photoacid Generator (A-3)

Charged were 2.2 parts of thianthrene, and 40 parts of glacial acetic acid in a reactor. Thereto was added dropwise 1.13 parts of 35% hydrogen peroxide and the reaction solution was stirred for 2 hours at 90° C. Then further, was added dropwise 0.05 parts of 35% hydrogen peroxide and the reaction solution was stirred for 30 minutes at 90° C. The reaction solution was poured into 100 parts of ion-exchanged water, filtrated under reduced pressure, and vacuum dried, so that solid product was obtained. Then, charged were 0.46 parts of the solid product, 10 parts of fluorobenzene, and 1.6 parts of aluminum chloride in a reactor, and stirred for 90 minutes under reflux. The reaction solution was cooled to room temperature and poured into 100 parts of ion-exchanged water. The mixture was extracted with 100 parts of dichloromethane, and the dichloromethane layer was washed with ion-exchanged water until the pH of the water layer became neutral. The dichloromethane layer was transferred to a rotary evaporator, and the solvent was removed by distillation, so that solid product was obtained. Then, charged were 0.17 parts of the solid product, and 5 parts of ethylene glycol in a reactor, and the solid product was dissolved at 120° C. Into the mixed solution, was added 0.05 parts of potassium hydroxide, and stirred for 1 hour. The reaction solution was poured into 100 parts of ion-exchanged water, and the mixture was extracted with 100 parts of dichloromethane, and the dichloromethane layer was washed with ion-exchanged water until the pH of the water layer became neutral. Into the dichloromethane layer, was added 0.38 parts of lithium tetrakis(pentafluorophenyl)gallate, and stirred for 1 hour. The dichloromethane layer was washed with ion-exchanged water three times by liquid-liquid separation, and then the dichloromethane layer was transferred to a rotary evaporator, and the solvent was removed by distillation, so that A-3 was obtained. The product was identified by $^1$H-NMR.

[Chemical Formula 28]

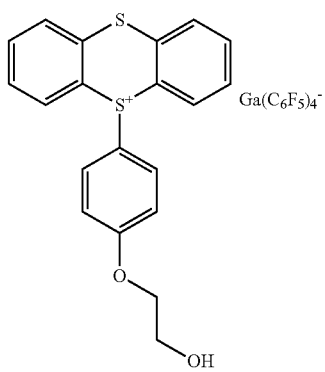

A-3

[Example 4] Synthesis of Photoacid Generator (A-4)

(A-4) was obtained as in Example 3, except that 0.38 parts of lithium tetrakis(pentafluorophenyl)gallate was replaced with 0.46 parts of lithium tetrakis(3,5-bis(trifluoromethyl)phenyl)gallate. The product was identified by $^1$H-NMR.

[Chemical Formula 29]

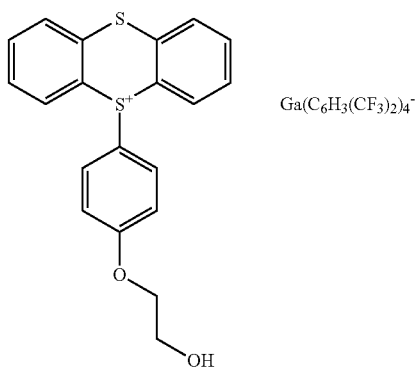

A-4

[Example 5] Synthesis of Photoacid Generator (A-5)

Charged were 4 parts of diphenylsulfoxide and 40 parts of dichloromethane in a reactor. Thereto was added dropwise 6.5 parts of trimethylsilyl chloride while maintaining the temperature at 20° C. or less. Then, thereto was added dropwise Grignard reagent prepared from 1.46 parts of metal magnesium, 12.42 parts of 2-bromonaphthalene, and 20 parts of tetrahydrofuran, and the reaction solution was stirred for 1 hour at 20° C. The reaction solution was poured into 100 parts of ion-exchanged water containing 1 part of 12N hydrochloric acid. The mixture was extracted with 100 parts of dichloromethane, and the dichloromethane layer was washed with ion-exchanged water until the pH of the water layer became neutral. Into the dichloromethane layer, was added 52.21 parts of lithium tetrakis(pentafluorophenyl) gallate, and stirred for 1 hour. The dichloromethane layer was washed with ion-exchanged water three times by liquid-liquid separation, and then the dichloromethane layer was transferred to a rotary evaporator, and the solvent was removed by distillation, so that A-5 was obtained. The product was identified by $^1$H-NMR.

[Chemical Formula 30]

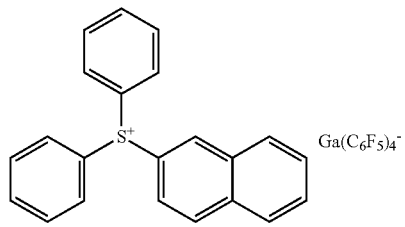

A-5

[Example 6] Synthesis of photoacid generator (A-6)

(A-6) was obtained as in Example 5, except that 52.21 parts of lithium tetrakis(pentafluorophenyl)gallate was replaced with 63.26 parts of lithium tetrakis(3,5-bis(trifluoromethyl)phenyl)gallate. The product was identified by $^1$H-NMR.

[Chemical Formula 31]

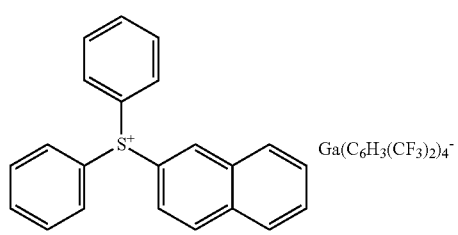

A-6

[Example 7] Synthesis of Photoacid Generator (A-7)

(A-7) was obtained as in Example 5, except that 12.42 parts of 2-bromonaphthalene was replaced with 15.43 parts of 9-bromoanthracene. The product was identified by $^1$H-NMR.

[Chemical Formula 32]

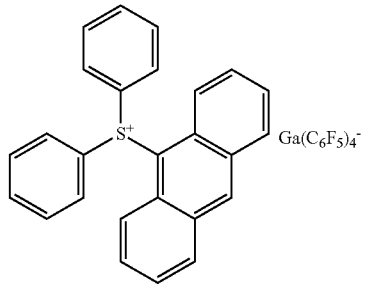

A-7

[Example 8] Synthesis of Photoacid Generator (A-8)

(A-8) was obtained as in Example 5, except that 12.42 parts of 2-bromonaphthalene was replaced with 15.43 parts of 9-bromoanthracene, and 52.21 parts of lithium tetrakis(pentafluorophenyl)gallate was replaced with 63.26 parts of lithium tetrakis(3,5-bis(trifluoromethyl)phenyl)gallate. The product was identified by $^1$H-NMR.

[Chemical Formula 33]

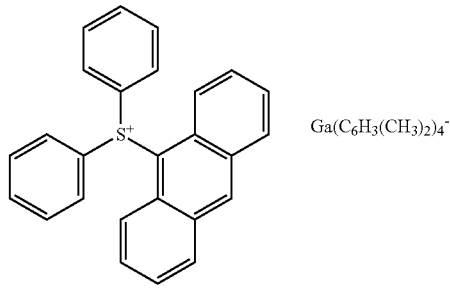

A-8

[Example 9] Synthesis of Photoacid Generator (A-9)

Charged were 1.6 parts of diphenylsulfoxide, 1.5 parts of diphenylsulfide, 2.5 parts of acetic anhydride, 1.5 parts of trifluoromethane sulfonic acid, and 15 parts of acetonitrile in a reactor, and stirred for 6 hours at 40° C. The reaction solution was cooled to room temperature, and poured into 60 parts of ion-exchanged water. The mixture was extracted with 50 parts of dichloromethane, and the dichloromethane layer was washed with ion-exchanged water until the pH of the water layer became neutral. The dichloromethane layer was transferred to a rotary evaporator, and the solvent was removed by distillation, so that a product was obtained. Thereto was added 25 parts of ethyl acetate, and the product was dissolved in a water bath at 60° C. Subsequently, after 100 parts of hexane was added and stirred, the operation of allowing the mixture to stand for 30 minutes at 5° C. and then removing the supernatant was performed twice to wash the product. The product was transferred to a rotary evaporator, and the solvent was removed by distillation, so that diphenyl[4-(phenylthio)phenyl]sulfonium triflate (triflate=trifluoromethanesulfonate anion) was obtained.
(Metathesis Process)

Poured were the triflate and 7.01 parts of lithium tetrakis(pentafluorophenyl)gallate into 40 parts of dichloromethane. Subsequently, the mixture was stirred at room temperature for 1 hour. After the dichloromethane layer was washed three times with ion-exchanged water by liquid-liquid separation, it was transferred to a rotary evaporator, and the solvent was removed by distillation, so that A-9 was obtained. The product was identified by $^1$H-NMR.

[Chemical Formula 34]

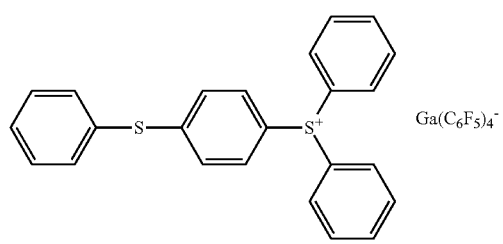

A-9

[Example 10] Synthesis of Photoacid Generator (A-10)

(A-10) was obtained as in Example 9, except that 7.01 parts of lithium tetrakis(pentafluorophenyl)gallate was replaced with 8.49 parts of lithium tetrakis(3,5-bis(trifluoromethyl)phenyl)gallate. The product was identified by $^1$H-NMR.

[Chemical Formula 35]

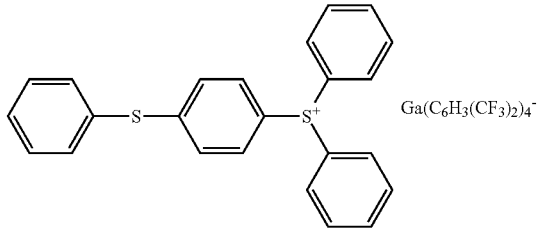

A-10

[Example 11] Synthesis of Photoacid Generator (A-11)

Charged were 160 parts of methane sulfonic acid, and 25 parts of phosphorus pentoxide in a reactor. Then, the reactor was replaced with nitrogen, and the solid mixture was dissolved by heating at 100° C. The reaction solution was cooled to room temperature. Thereto was added 44 parts of bis(4-methoxyphenyl)sulfoxide, and 43 parts of phenylether, and then stirred for 3 hours under water cooling. Subsequently, the reaction solution was poured into 1000 parts of ice-water, stirred for 1 hour, and the operation of allowing the mixture to stand. After removing the upper layer, 1000 parts of dichloromethane was added to the lower layer, and the dichloromethane layer was washed with ion-exchanged water until the pH of the water layer became neutral. Into the dichloromethane layer, was added 146.56 parts of lithium tetrakis(pentafluorophenyl)gallate, and stirred for 1 hour. The dichloromethane layer was washed with ion-exchanged water three times by liquid-liquid separation, and then the dichloromethane layer was transferred to a rotary evaporator, and the solvent was removed by distillation, so that A-11 was obtained. The product was identified by $^1$H-NMR.

[Chemical Formula 36]

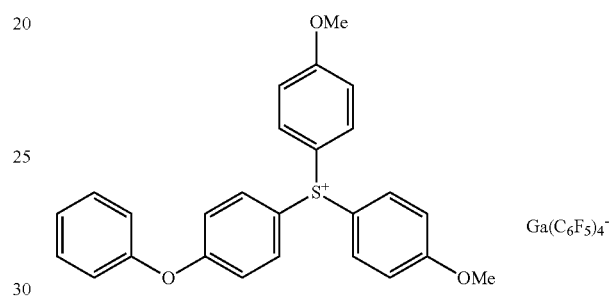

A-11

[Example 12] Synthesis of Photoacid Generator (A-12)

(A-12) was obtained as in Example 11, except that 146.56 parts of lithium tetrakis(pentafluorophenyl)gallate was replaced with 177.51 parts of lithium tetrakis(3,5-bis(trifluoromethyl)phenyl)gallate. The product was identified by $^1$H-NMR.

[Chemical Formula 37]

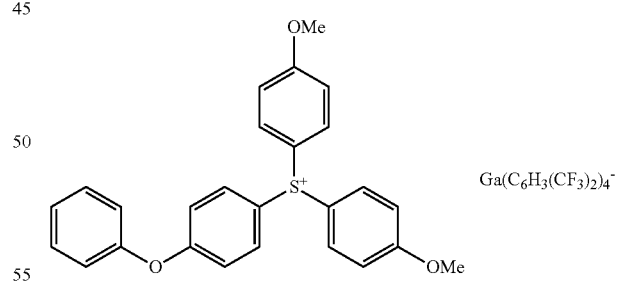

A-12

[Example 13] Synthesis of Photoacid Generator (A-13)

Charged were 65.44 parts of methane sulfonic acid, and 6.44 parts of phosphorus pentoxide in a reactor. Then, the reactor was replaced with nitrogen, and the solid mixture was dissolved by heating at 100° C. The reaction solution was cooled to room temperature. Thereto was added 9.50 parts of N-methylacridine, and 10.63 parts of bis(4-hydroxyphenyl)sulfoxide, and then stirred for 4 hours at 50° C.

Subsequently, a mixture of 180 parts of ice-water, 190 parts of methanol, and 110 parts of isopropylether was poured into the reaction solution, stirred for 1 hour, and the operation of allowing the mixture to stand. After removing the upper layer, 370 parts of dichloromethane was added to the lower layer, and the dichloromethane layer was washed with ion-exchanged water until the pH of the water layer became neutral. Into the dichloromethane layer, was added 59.44 parts of lithium tetrakis(pentafluorophenyl)gallate, and stirred for 1 hour. The dichloromethane layer was washed with ion-exchanged water three times by liquid-liquid separation, and then the dichloromethane layer was transferred to a rotary evaporator, and the solvent was removed by distillation, so that A-13 was obtained. The product was identified by $^1$H-NMR.

[Chemical Formula 38]

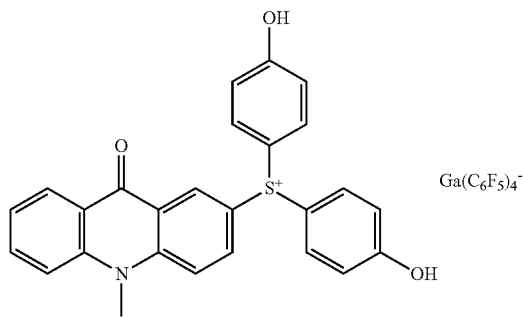

A-13

[Example 14] Synthesis of Photoacid Generator (A-14)

(A-14) was obtained as in Example 13, except that 59.44 parts of lithium tetrakis(pentafluorophenyl)gallate was replaced with 72.01 parts of lithium tetrakis(3,5-bis(trifluoromethyl)phenyl)gallate. The product was identified by $^1$H-NMR.

[Chemical Formula 39]

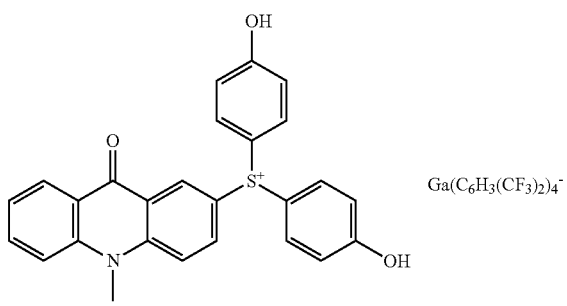

A-14

[Example 15] Synthesis of Photoacid Generator (A-15)

(A-15) was obtained as in Example 13, except that 9.50 parts of N-methylacridine was replaced with 9.45 parts of anthraquinone, and 10.63 parts of bis(4-hydroxyphenyl) sulfoxide was replaced with 10.82 parts of bis(4-fluorophenyl)sulfoxide. The product was identified by $^1$H-NMR.

[Chemical Formula 40]

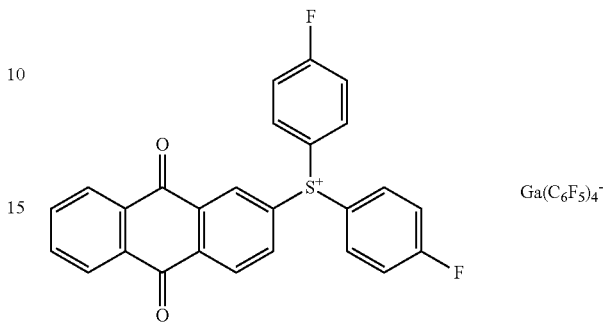

A-15

[Example 16] Synthesis of Photoacid Generator (A-16)

(A-16) was obtained as in Example 13, except that 9.50 parts of N-methylacridine was replaced with 9.45 parts of anthraquinone, 10.63 parts of bis(4-hydroxyphenyl)sulfoxide was replaced with 10.82 parts of bis(4-fluorophenyl)sulfoxide, and 59.44 parts of lithium tetrakis(pentafluorophenyl)gallate was replaced with 68.52 parts of lithium tetrakis(3,5-bis(trifluoromethyl)phenyl)gallate. The product was identified by $^1$H-NMR.

[Chemical Formula 41]

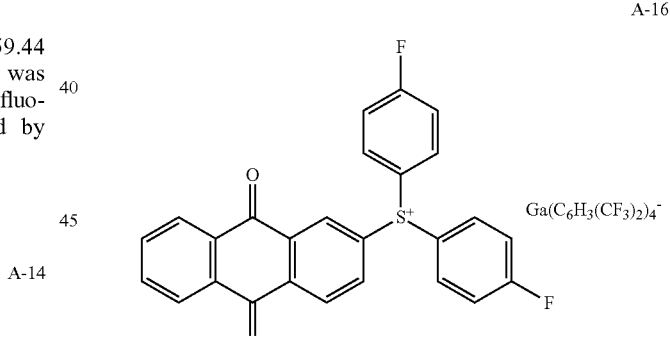

A-16

[Example 17] Synthesis of Photoacid Generator (A-17)

Charged were 19.9 parts of phenothiazine, 24 parts of (4-fluorophenyl)sulfoxide, 50 parts of acetic anhydride, and 200 parts of methane sulfonic acid in a reactor, stirred for about 8 hours at 80° C. The reaction solution was cooled to room temperature, and poured into 400 parts of ion-exchanged water. The mixture was extracted with 400 parts of dichloromethane, and the dichloromethane layer was washed with ion-exchanged water until the pH of the water layer became neutral. Into the dichloromethane layer, was added 81.91 parts of lithium tetrakis(pentafluorophenyl) gallate, and stirred for 1 hour. The dichloromethane layer was washed with ion-exchanged water three times by liquid-liquid separation, and then the dichloromethane layer was transferred to a rotary evaporator, and the solvent was removed by distillation, so that A-17 was obtained. The product was identified by ¹H-NMR.

[Chemical Formula 42]

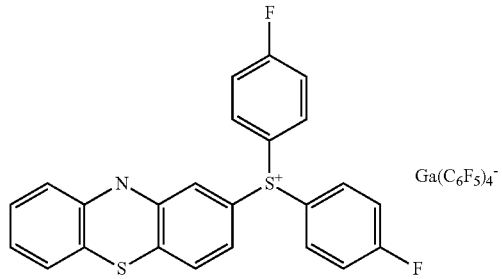

A-17

[Example 18] Synthesis of Photoacid Generator (A-18)

(A-18) was obtained as in Example 17, except that 81.91 parts of lithium tetrakis(pentafluorophenyl)gallate was replaced with 99.24 parts of lithium tetrakis(3,5-bis(trifluoromethyl)phenyl)gallate. The product was identified by ¹H-NMR.

[Chemical Formula 43]

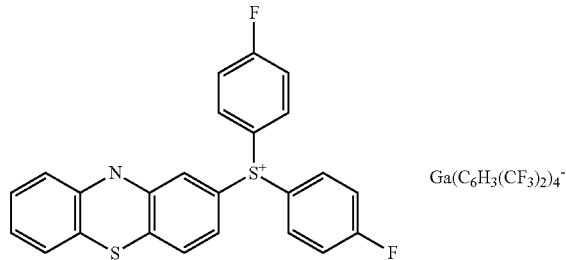

A-18

[Example 19] Synthesis of Photoacid Generator (A-19)

Charged were 14.41 parts of methane sulfonic acid, and 14.19 parts of phosphorus pentoxide in a reactor. Then, the reactor was replaced with nitrogen, and the solid mixture was dissolved by heating at 100° C. The reaction solution was cooled to room temperature. Thereto was added 23.4 parts of bis(4-hydroxyphenyl)sulfoxide, and 35 parts of 9,9-bis(4-hydroxyphenyl)-9H-fluorene, and then stirred for 2 hours at 15° C. Subsequently, the reaction solution was poured into a mixture of 500 parts of ice-water, and 250 parts of methanol, so that a precipitated solid product was obtained by filtration. A mixture of 400 parts of methylisobutylketone, and 300 parts of ion-exchanged water was poured into the solid product, and the solution was stirred for 1 hour at room temperature. Into the methylisobutylketone layer, was added 87.87 parts of lithium tetrakis(pentafluorophenyl)gallate, and stirred for 1 hour at room temperature. The methylisobutylketone layer was washed with ion-exchanged water three times by liquid-liquid separation, and then the methylisobutylketone layer was transferred to a rotary evaporator, and the solvent was removed by distillation, so that A-19 was obtained. The product was identified by ¹H-NMR.

[Chemical Formula 44]

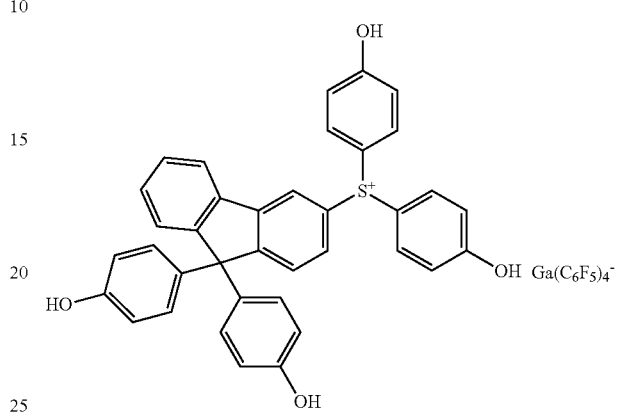

A-19

[Example 20] Synthesis of Photoacid Generator (A-20)

(A-20) was obtained as in Example 19, except that 87.87 parts of lithium tetrakis(pentafluorophenyl)gallate was replaced with 106.47 parts of lithium tetrakis(3,5-bis(trifluoromethyl)phenyl)gallate. The product was identified by ¹H-NMR.

[Chemical Formula 45]

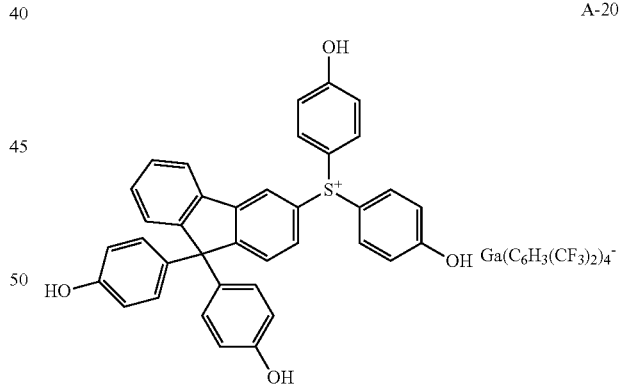

A-20

[Example 21] Synthesis of Photoacid Generator (A-21)

Charged were 27.03 parts of methane sulfonic acid, and 2.65 parts of phosphorus pentoxide in a reactor. Then, the reactor was replaced with nitrogen, and the solid mixture was dissolved by heating at 100° C. The reaction solution was cooled to room temperature. Thereto was added 3.66 parts of N-ethylcarbazole, and then added dropwise 4.47 parts of bis(4-fluorophenyl)sulfoxide dissolved in 8.3 parts of chlorobenzene, and then stirred for 1 hour at 46° C.

Subsequently, a mixture of 100 parts of ion-exchanged water, and 40 parts of methanol was poured into the reaction solution, and then 350 parts of diisopropylether and 40 parts of acetone was added into the reaction solution, stirred, and the operation of allowing the mixture to stand. After removing the upper layer, 200 parts of dichloromethane was added to the lower layer, and the dichloromethane layer was washed with ion-exchanged water until the pH of the water layer became neutral. Into the dichloromethane layer, was added 63 parts of lithium tetrakis(pentafluorophenyl)gallate, and stirred for 1 hour. The dichloromethane layer was washed with ion-exchanged water three times by liquid-liquid separation, and then the dichloromethane layer was transferred to a rotary evaporator, and the solvent was removed by distillation, so that A-21 was obtained. The product was identified by $^1$H-NMR.

[Chemical Formula 46]

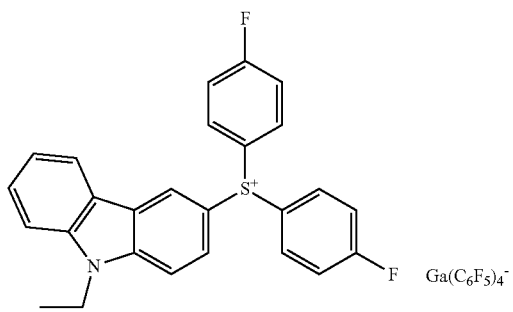

A-21

[Example 22] Synthesis of Photoacid Generator (A-22)

(A-22) was obtained as in Example 21, except that 63 parts of lithium tetrakis(pentafluorophenyl)gallate was replaced with 54.02 parts of lithium tetrakis(3,5-bis(trifluoromethyl)phenyl)gallate. The product was identified by $^1$H-NMR.

[Chemical Formula 47]

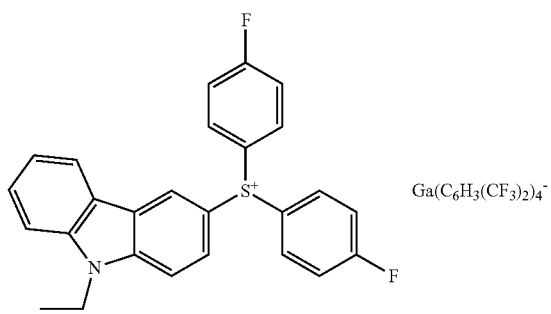

A-22

[Example 23] Synthesis of Photoacid Generator (A-23)

Added were 32.87 parts of 2-acetyldibenzothiophene-5-oxide, and 15.6 parts of fluorobenzene into 200 parts of ice-cooled concentrated sulfuric acid in a reactor, stirred for 2 hours at 15° C. Subsequently, the reaction solution was poured into a mixture of 200 parts of ice-water, 200 parts of methanol, and 200 parts of toluene. After removing the upper layer, 300 parts of dichloromethane was added to the lower layer, and the dichloromethane layer was washed with ion-exchanged water until the pH of the water layer became neutral. Into the dichloromethane layer, was added 136 parts of lithium tetrakis(pentafluorophenyl)gallate, and stirred for 1 hour. The dichloromethane layer was washed with ion-exchanged water three times by liquid-liquid separation, and then the dichloromethane layer was transferred to a rotary evaporator, and the solvent was removed by distillation, so that A-23 was obtained. The product was identified by $^1$H-NMR.

[Chemical Formula 48]

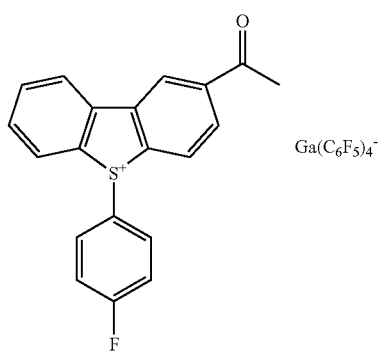

A-23

[Example 24] Synthesis of Photoacid Generator (A-24)

(A-24) was obtained as in Example 23, except that 136 parts of lithium tetrakis(pentafluorophenyl)gallate was replaced with 165 parts of lithium tetrakis(3,5-bis(trifluoromethyl)phenyl)gallate. The product was identified by $^1$H-NMR.

[Chemical Formula 49]

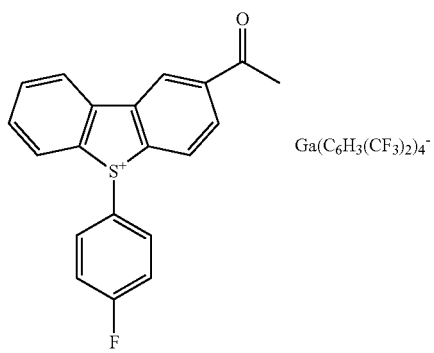

A-24

[Example 25] Synthesis of Photoacid Generator (A-25)

Charged were 600 parts of dichloromethane, 93.3 parts of aluminum chloride, 107.5 parts of dibenzothiophene, and 82.0 parts of benzoyl chloride in a reactor, and stirred for 2 hours at room temperature. Then, the reaction solution was poured into 1000 parts of ice-water. The dichloromethane layer was washed with ion-exchanged water until the pH of the water layer became neutral, and then transferred to a rotary evaporator, and the solvent was removed by distillation, so that a product was obtained. Subsequently, 47.7 parts of di-p-fluorophenylsulfoxide, and 57.6 parts of the product obtained above were added into 295 parts of 95% sulfuric acid under stirring, and the reaction solution was stirred for 10 hours at room temperature. Then, the reaction solution was poured into a mixture solution of 500 parts of ice-water, 600 parts of methanol, and 300 parts of toluene. After removing the upper layer, 500 parts of dichloromethane was added to the lower layer, and the dichloromethane layer was washed with ion-exchanged water until the pH of the water layer became neutral. Into the dichloromethane layer, was added 136 parts of lithium tetrakis(pentafluorophenyl)gallate, and stirred for 1 hour. The dichloromethane layer was washed with ion-exchanged water three times by liquid-liquid separation, and then the dichloromethane layer was transferred to a rotary evaporator, and the solvent was removed by distillation, so that A-25 was obtained. The product was identified by $^1$H-NMR.

[Chemical Formula 50]

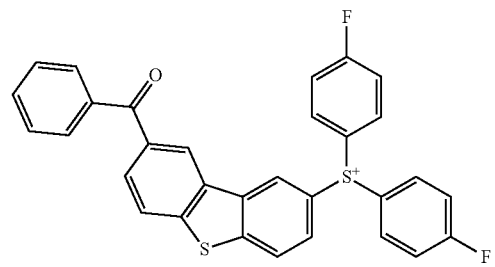

A-25

[Example 26] Synthesis of Photoacid Generator (A-26)

(A-26) was obtained as in Example 25, except that 136 parts of lithium tetrakis(pentafluorophenyl)gallate was replaced with 165 parts of lithium tetrakis(3,5-bis(trifluoromethyl)phenyl)gallate. The product was identified by $^1$H-NMR.

[Chemical Formula 51]

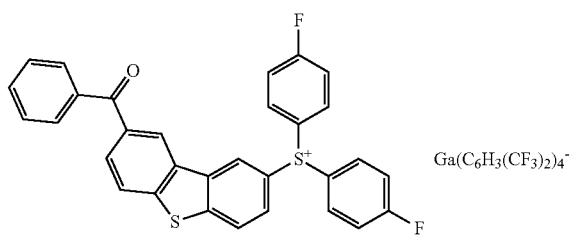

A-26

[Example 27] Synthesis of Photoacid Generator (A-27)

Charged were 8.81 parts of 7-methoxycoumarin, 11.91 parts of bis(4-fluorophenyl)sulfoxide, and 30 parts of polyphosphoric acid in a reactor, and stirred for 6 hours at 120° C. The reaction solution was cooled to room temperature, and poured into 200 parts of ion-exchanged water. The mixture was extracted with 200 parts of dichloromethane, and the dichloromethane layer was washed with ion-exchanged water until the pH of the water layer became neutral. Into the dichloromethane layer, was added 32.63 parts of lithium tetrakis(pentafluorophenyl)gallate, and stirred for 1 hour. The dichloromethane layer was washed with ion-exchanged water three times by liquid-liquid separation, and then the dichloromethane layer was transferred to a rotary evaporator, and the solvent was removed by distillation, so that A-27 was obtained. The product was identified by $^1$H-NMR.

[Chemical Formula 52]

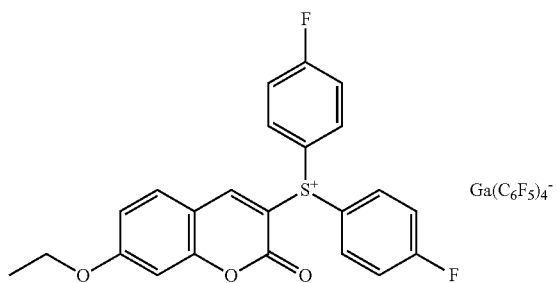

A-27

[Example 28] Synthesis of Photoacid Generator (A-28)

(A-28) was obtained as in Example 27, except that 32.63 parts of lithium tetrakis(pentafluorophenyl)gallate was replaced with 39.54 parts of lithium tetrakis(3,5-bis(trifluoromethyl)phenyl)gallate. The product was identified by $^1$H-NMR.

[Chemical Formula 53]

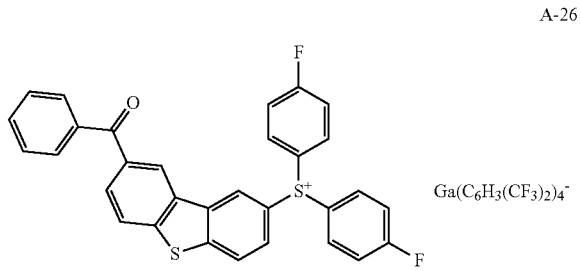

A-28

[Example 29] Synthesis of Photoacid Generator (A-29)

Charged were 4.6 parts of bis(4-methylphenyl) sulfoxide, 3.2 parts of 2-phenylthiophene and 10.2 parts of acetic anhydride in a reactor. Thereto was added 7.7 parts of methane sulfonic acid while maintaining the temperature at 10° C. or less, stirred for 3 hours, and then stirred for 4 hours at room temperature. The reaction solution was poured into 100 parts of ion-exchanged water. The mixture was extracted with 100 parts of dichloromethane, and the dichloromethane layer was washed with ion-exchanged water until the pH of the water layer became neutral. Into the dichloromethane layer, was added 17.4 parts of lithium tetrakis(pentafluorophenyl)gallate, and stirred for 1 hour. The dichloromethane layer was washed with ion-exchanged water three times by liquid-liquid separation, and then the dichloromethane layer was transferred to a rotary evaporator, and the solvent was removed by distillation, so that A-29 was obtained. The product was identified by $^1$H-NMR.

[Chemical Formula 54]

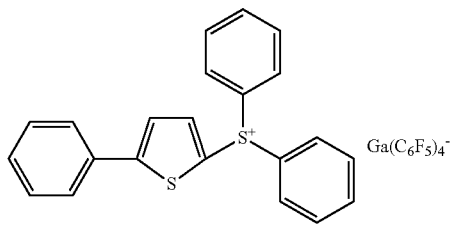

A-29

[Chemical Formula 55]

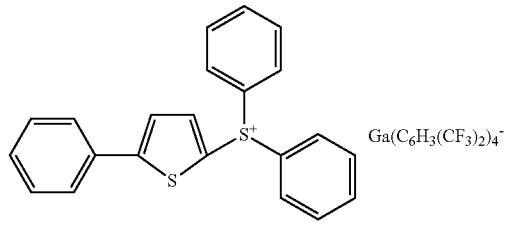

A-30

[Example 31] Synthesis of Photoacid Generator (A-31)

Charged were 31.71 parts of methane sulfonic acid, and 3.41 parts of phosphorus pentoxide in a reactor. Then, the reactor was replaced with nitrogen, and the solid mixture was dissolved by heating at 100° C. The reaction solution was cooled to room temperature. Thereto was added 26.3 parts of bis(4-hydroxyethoxyphenyl)sulfide, and 3.07 parts of diphenylsulfide, and then stirred for 5 hours at room temperature. The reaction solution was poured into 400 parts of ion-exchanged water. The mixture was extracted with 200 parts of dichloromethane, and the dichloromethane layer was washed with ion-exchanged water until the pH of the water layer became neutral. Into the dichloromethane layer, was added 14.34 parts of lithium tetrakis(pentafluorophenyl)gallate, and stirred for 1 hour. The dichloromethane layer was washed with ion-exchanged water three times by liquid-liquid separation, and then the dichloromethane layer was transferred to a rotary evaporator, and the solvent was removed by distillation, so that A-31 was obtained. The product was identified by $^1$H-NMR.

[Chemical Formula 56]

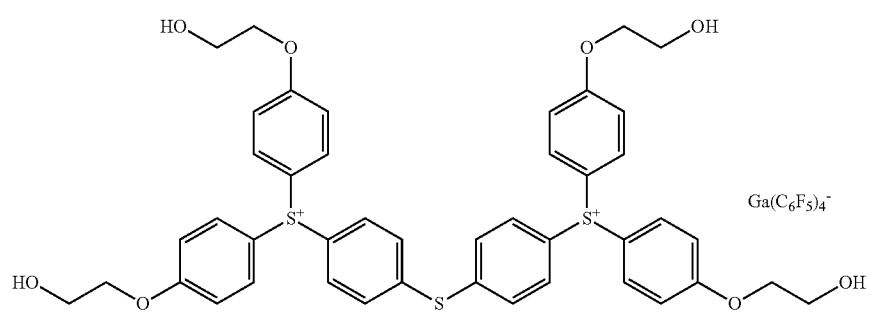

A-31

[Example 30] Synthesis of Photoacid Generator (A-30)

(A-30) was obtained as in Example 29, except that 17.4 parts of lithium tetrakis(pentafluorophenyl)gallate was replaced with 21.08 parts of lithium tetrakis(3,5-bis(trifluoromethyl)phenyl)gallate. The product was identified by $^1$H-NMR.

[Example 32] Synthesis of Photoacid Generator (A-32)

(A-32) was obtained as in Example 31, except that 14.34 parts of lithium tetrakis(pentafluorophenyl)gallate was replaced with 17.37 parts of lithium tetrakis(3,5-bis(trifluoromethyl)phenyl)gallate. The product was identified by $^1$H-NMR.

[Chemical Formula 57]

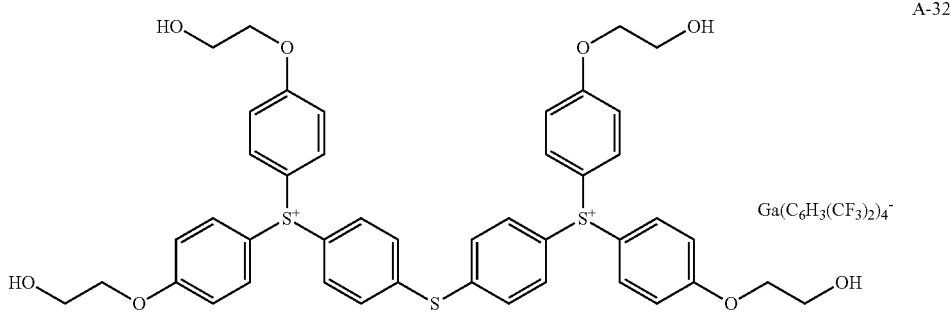

A-32

[Example 33] Synthesis of Photoacid Generator
(A-33)

Charged were 24.27 parts of p-bromoacetophenone, 15.35 parts of sodium carbonate and 50 parts of dichloromethane in a reactor. Thereto was added dropwise 15.9 parts of thiophenol, stirred for 6 hours at 35° C. The reaction solution was poured into 200 parts of ice-water. The mixture was extracted with 50 parts of ethyl acetate, and the ethyl acetate layer was transferred to a rotary evaporator, and the solvent was removed by distillation, so that a product was obtained. A solution of 11.69 parts of the product obtained above dissolved in 20 parts of dichloromethane was added dropwise at 0° C. into a mixture solution of 12.86 parts of aluminum chloride suspended in 40 parts of dichloromethane. Then, 1.85 parts of thionyl chloride was added dropwise at −5° C. into a reaction mixture solution. The reaction mixture solution was stirred for 5 hours at room temperature, poured on ice. After removing the upper layer, the dichloromethane layer was washed with ion-exchanged water until the pH of the water layer became neutral. Into the dichloromethane layer, was added 13.54 parts of lithium tetrakis (pentafluorophenyl)gallate, and stirred for 1 hour. The dichloromethane layer was washed with ion-exchanged water three times by liquid-liquid separation, and then the dichloromethane layer was transferred to a rotary evaporator, and the solvent was removed by distillation, so that A-33 was obtained. The product was identified by $^1$H-NMR.

[Chemical Formula 58]

A-33

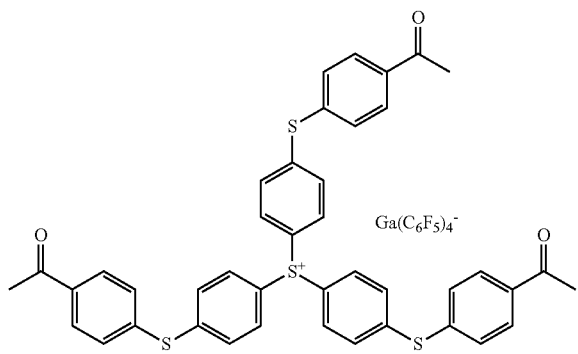

[Example 34] Synthesis of Photoacid Generator
(A-34)

(A-34) was obtained as in Example 33, except that 13.54 parts of lithium tetrakis(pentafluorophenyl)gallate was replaced with 16.4 parts of lithium tetrakis(3,5-bis(trifluoromethyl)phenyl)gallate. The product was identified by $^1$H-NMR.

[Chemical Formula 59]

A-34

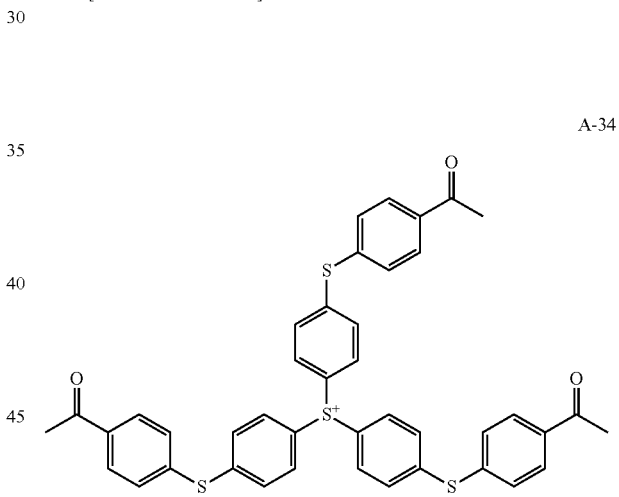

[Example 35] Synthesis of Heatacid Generator
(A-35)

Added were 1.59 parts of 4-hydroxyphenyl-methyl-1-naphthylmethylsulfonium chloride, and 4.36 parts of lithium tetrakis(pentafluorophenyl)gallate into 30 parts of dichloromethane in a reactor, stirred for 3 hours at room temperature. The dichloromethane layer was washed with ion-exchanged water three times by liquid-liquid separation, and then the dichloromethane layer was transferred to a rotary evaporator, and the solvent was removed by distillation, so that A-35 was obtained. The product was identified by $^1$H-NMR.

[Chemical Formula 60]

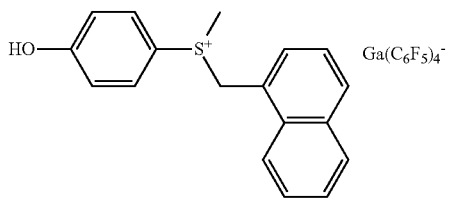

A-35

[Example 36] Synthesis of Heatacid Generator (A-36)

(A-36) was obtained as in Example 35, except that 4.36 parts of lithium tetrakis(pentafluorophenyl)gallate was replaced with 5.28 parts of lithium tetrakis(3,5-bis(trifluoromethyl)phenyl)gallate. The product was identified by ¹H-NMR.

[Chemical Formula 61]

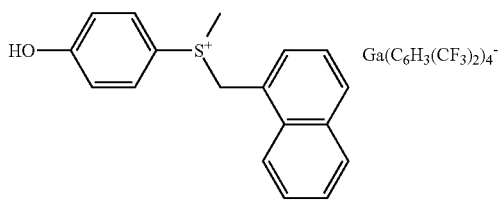

A-36

[Example 37] Synthesis of Heatacid Generator (A-37)

Added were 1.59 parts of 4-hydroxyphenyl-methyl-1-benzylsulfonium chloride, and 4.36 parts of lithium tetrakis(pentafluorophenyl)gallate into 30 parts of dichloromethane in a reactor, stirred for 3 hours at room temperature. The dichloromethane layer was washed with ion-exchanged water three times by liquid-liquid separation, and then the dichloromethane layer was transferred to a rotary evaporator, and the solvent was removed by distillation, so that A-37 was obtained. The product was identified by ¹H-NMR.

[Chemical Formula 62]

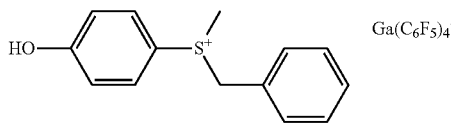

A-37

[Example 38] Synthesis of Heatacid Generator (A-38)

(A-38) was obtained as in Example 37, except that 4.36 parts of lithium tetrakis(pentafluorophenyl)gallate was replaced with 5.28 parts of lithium tetrakis(3,5-bis(trifluoromethyl)phenyl)gallate. The product was identified by ¹H-NMR.

[Chemical Formula 63]

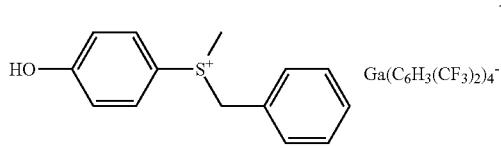

A-38

[Example 39] Synthesis of Heatacid Generator (A-39)

Added were 1.08 parts of p-nitrobenzyl bromide, and 0.7 parts of 4-(methyl)thiophenol into 20 parts of methanol in a reactor, stirred for 12 hours at 50° C. Then, added were 30 parts of ion-exchanged water, and 20 parts of ethyl acetate into the reaction solution, stirred for 30 minutes, and separated the solution. Then, the ethyl acetate layer was removed. Poured were 4.36 parts of lithium tetrakis(pentafluorophenyl)gallate, and 40 parts of ethyl acetate into the water layer, stirred for 3 hours at room temperature. The ethyl acetate layer was washed with ion-exchanged water three times by liquid-liquid separation, and then the dichloromethane layer was transferred to a rotary evaporator, and the solvent was removed by distillation, so that A-39 was obtained. The product was identified by ¹H-NMR.

[Chemical Formula 64]

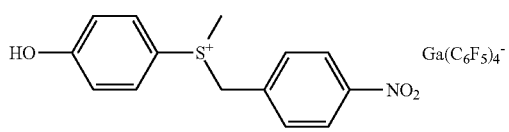

A-39

[Example 40] Synthesis of Heatacid Generator (A-40)

(A-40) was obtained as in Example 39, except that 4.36 parts of lithium tetrakis(pentafluorophenyl)gallate was replaced with 5.28 parts of lithium tetrakis(3,5-bis(trifluoromethyl)phenyl)gallate. The product was identified by ¹H-NMR.

[Chemical Formula 65]

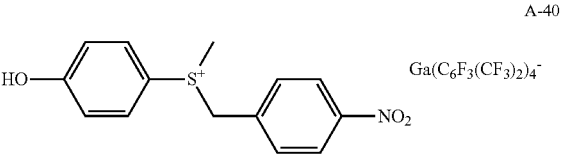

A-40

[Example 41] Synthesis of Heatacid Generator (A-41)

Added was 0.95 parts of 4-hydroxyphenyldimethylsulfonium chloride into 30 parts of acetonitrile in a reactor. Then, added was 0.61 parts of triethylamine at 10° C. or less, and after 30 minutes added dropwise 0.47 parts of acetyl chloride. After stirring for 3 hours, a hydrochloride salt of triethylamine as a by-product was removed by filtration.

Poured was 4.36 parts of lithium tetrakis(pentafluorophenyl)gallate into the acetonitrile layer, stirred for 3 hours at room temperature. The acetonitrile layer was washed with ion-exchanged water three times by liquid-liquid separation, and then the acetonitrile layer was transferred to a rotary evaporator, and the solvent was removed by distillation, so that A-41 was obtained. The product was identified by ¹H-NMR.

[Chemical Formula 66]

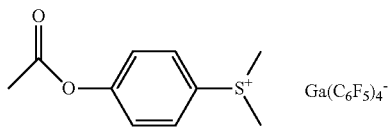

[Example 42] Synthesis of Heatacid Generator (A-42)

(A-42) was obtained as in Example 41, except that 4.36 parts of lithium tetrakis(pentafluorophenyl)gallate was replaced with 5.28 parts of lithium tetrakis(3,5-bis(trifluoromethyl)phenyl)gallate. The product was identified by ¹H-NMR.

[Chemical Formula 67]

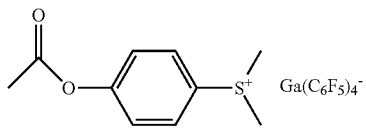

[Comparative Example 1] Synthesis of Photoacid Generator (A-43)

(A-43) was obtained as in Example 9, except that 7.01 parts of lithium tetrakis(pentafluorophenyl)gallate was replaced with 2.21 parts of potassium hexafluoroantimonate. The product was identified by ¹H-NMR.

[Chemical Formula 68]

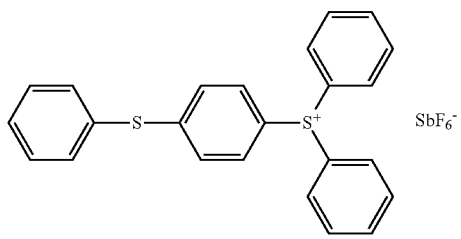

[Comparative Example 2] Synthesis of Photoacid Generator (A-44)

(A-44) was obtained as in Example 9, except that 7.01 parts of lithium tetrakis(pentafluorophenyl)gallate was replaced with 5.79 parts of potassium terakis(pentafluorophenyl)borate. The product was identified by ¹H-NMR.

[Chemical Formula 69]

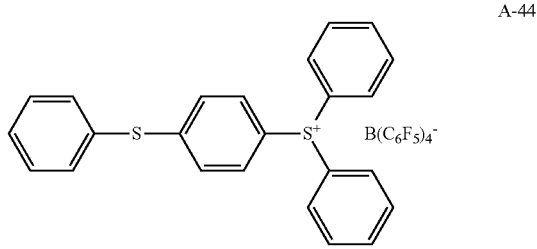

[Comparative Example 3] Synthesis of Photoacid Generator (A-45)

(A-45) was obtained as in Example 9, except that 7.01 parts of lithium tetrakis(pentafluorophenyl)gallate was replaced with 1.48 parts of potassium hexafluorophosphate. The product was identified by ¹H-NMR.

[Chemical Formula 70]

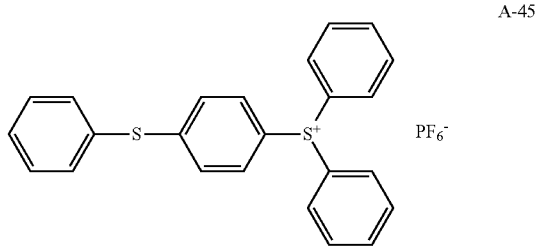

[Comparative Example 4] Synthesis of Heatacid Generator (A-46)

(A-46) was obtained as in Example 35, except that 4.36 parts of lithium tetrakis(pentafluorophenyl)gallate was replaced with 1.38 parts of potassium hexafluoroantimonate. The product was identified by ¹H-NMR.

[Chemical Formula 71]

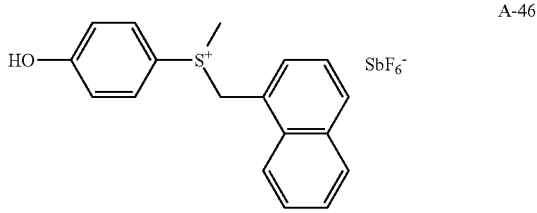

[Comparative Example 5] Synthesis of Heatacid Generator (A-47)

(A-47) was obtained as in Example 35, except that 4.36 parts of lithium tetrakis(pentafluorophenyl)gallate was replaced with 3.6 parts of potassium terakis(pentafluorophenyl)borate. The product was identified by ¹H-NMR.

[Chemical Formula 72]

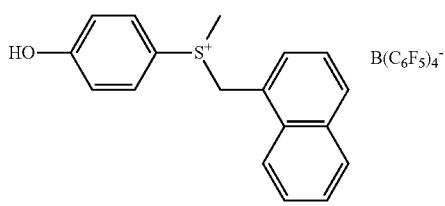

A-47

[Comparative Example 6] Synthesis of Heatacid Generator (A-48)

(A-48) was obtained as in Example 35, except that 4.36 parts of lithium tetrakis(pentafluorophenyl)gallate was replaced with 0.92 parts of potassium hexafluorophosphate. The product was identified by $^1$H-NMR.

[Chemical Formula 73]

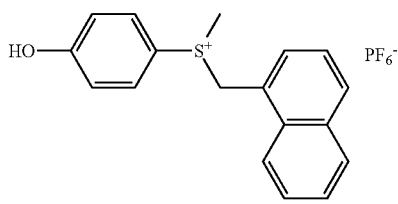

A-48

[Evaluation]
(Preparation of Heat- or Energy Ray-Curable Composition)

The heat- or photo-acid generator of the present invention and comparative compounds, an epoxide (3,4-epoxycyclohexylmethyl-3,4-epoxycyclohexane carboxylate, CELLOXIDE 2021 P manufactured by Daicel Chemical Industries, Ltd.) as a cationic polymerizable compound and bisphenol A (4,4'-(propane-2,2-diyl)diphenol manufactured by Idemitsu Kosan Co., Ltd) were uniformly mixed in an amount formulated as shown in Table 1 to prepare each of energy ray-curable compositions 1 to 42 of the present invention and comparative curable compositions 43 to 48.

TABLE 1

| No. | acid generator | Amount of acid generator formulated | Epoxide | Bisphenol A |
|---|---|---|---|---|
| 1 | A-1 | 2 | 100 | 5 |
| 2 | A-2 | 2 | 100 | 5 |
| 3 | A-3 | 2 | 100 | 5 |
| 4 | A-4 | 2 | 100 | 5 |
| 5 | A-5 | 2 | 100 | 5 |
| 6 | A-6 | 2 | 100 | 5 |
| 7 | A-7 | 2 | 100 | 5 |
| 8 | A-8 | 2 | 100 | 5 |
| 9 | A-9 | 2 | 100 | 5 |
| 10 | A-10 | 2 | 100 | 5 |
| 11 | A-11 | 2 | 100 | 5 |
| 12 | A-12 | 2 | 100 | 5 |
| 13 | A-13 | 2 | 100 | 5 |
| 14 | A-14 | 2 | 100 | 5 |
| 15 | A-15 | 2 | 100 | 5 |
| 16 | A-16 | 2 | 100 | 5 |
| 17 | A-17 | 2 | 100 | 5 |
| 18 | A-18 | 2 | 100 | 5 |

TABLE 1-continued

| No. | acid generator | Amount of acid generator formulated | Epoxide | Bisphenol A |
|---|---|---|---|---|
| 19 | A-19 | 2 | 100 | 5 |
| 20 | A-20 | 2 | 100 | 5 |
| 21 | A-21 | 2 | 100 | 5 |
| 22 | A-22 | 2 | 100 | 5 |
| 23 | A-23 | 2 | 100 | 5 |
| 24 | A-24 | 2 | 100 | 5 |
| 25 | A-25 | 2 | 100 | 5 |
| 26 | A-26 | 2 | 100 | 5 |
| 27 | A-27 | 2 | 100 | 5 |
| 28 | A-28 | 2 | 100 | 5 |
| 29 | A-29 | 2 | 100 | 5 |
| 30 | A-30 | 2 | 100 | 5 |
| 31 | A-31 | 2 | 100 | 5 |
| 32 | A-32 | 2 | 100 | 5 |
| 33 | A-33 | 2 | 100 | 5 |
| 34 | A-34 | 2 | 100 | 5 |
| 35 | A-35 | 2 | 100 | 5 |
| 36 | A-36 | 2 | 100 | 5 |
| 37 | A-37 | 2 | 100 | 5 |
| 38 | A-38 | 2 | 100 | 5 |
| 39 | A-39 | 2 | 100 | 5 |
| 40 | A-40 | 2 | 100 | 5 |
| 41 | A-41 | 2 | 100 | 5 |
| 42 | A-42 | 2 | 100 | 5 |
| 43 | A-43 | 2 | 100 | 5 |
| 44 | A-44 | 2 | 100 | 5 |
| 45 | A-45 | 2 | 100 | 5 |
| 46 | A-46 | 2 | 100 | 5 |
| 47 | A-47 | 2 | 100 | 5 |
| 48 | A-48 | 2 | 100 | 5 |

<Photosensitivity (Photo-Curability) Evaluation>

The energy ray-curable compositions 1 to 34 of the present invention and comparative energy ray-curable compositions 43 to 45 obtained above were applied to a polyethylene terephthalate (PET) film using an applicator with a film thickness of 40 μm. Using an ultraviolet irradiator, the PET film was irradiated with ultraviolet light whose wavelength was restricted with filters. The filters used were 365 Filter (manufactured by EYE GRAPHICS Co., Ltd., a filter for cutting off light with wavelengths of less than 365 nm). Forty minutes after the irradiation, the pencil hardness (JIS K 5600-5-4: 1999) of the coating film hardness was measured and evaluated according to the criteria below (the coating film had a thickness of about 40 m after the curing).
(Evaluation Criteria)
  ⊙: The pencil hardness is 2H or higher.
  ○: The pencil hardness is from H to B.
  Δ: The pencil hardness is from 2B to 4B.
  x: Due to liquidness or tackiness, it is not possible to measure the pencil hardness.
(Ultraviolet Light Irradiation Conditions)
  Ultraviolet ray irradiator: belt conveyor-type UV irradiator (manufactured by EYE GRAPHICS Co., Ltd.)
  Lamp: 1.5 kW high-pressure mercury lamp
  Filter: 365 Filter (manufactured by EYE GRAPHICS Co., Ltd.)
  Irradiance (measured with a 365 nm head photometer): 100 mW/cm$^2$
  Integral light dose (measured with a 365 nm head photometer): 300 mJ/cm$^2$
<Heat Resistance (Yellowing) Test>

The energy ray-curable compositions 1 to 34 of the present invention and comparative energy ray-curable compositions 43 to 45 obtained above were applied onto a slide glass with a thickness of 40 m by an applicator. Using an ultraviolet irradiator, the above-mentioned coated slide glass was irradiated with ultraviolet light.
(Ultraviolet Light Irradiation Conditions)
Ultraviolet ray irradiator: belt conveyor-type UV irradiator (manufactured by EYE GRAPHICS Co., Ltd.)
Lamp: 1.5 kW high-pressure mercury lamp
Irradiance (measured with a 365 nm head photometer): 100 mW/cm$^2$
Integral light dose (measured with a 365 nm head photometer): 1000 mJ/cm$^2$ After the irradiation, the composition was cured at room temperature for 40 minutes, and then post-cured on a hot plate at 120° C. for 30 minutes to prepare a heat resistance test sample. The sample was heated for 15 minutes on a hot plate controlled to a temperature of 240° C., and the color of the coating film was visually evaluated. Evaluation criteria are as follows.
(Evaluation Criteria)
⊙: Colorless (yellowing of coating film does not occur)
○: Pale yellow or yellow
x: Brown
<Metal Erosion Test>

The energy ray-curable compositions 1 to 34 of the present invention and comparative energy ray-curable compositions 43 to 45 obtained above were applied onto Cu board with a thickness of 40 μm by an applicator. Using an ultraviolet irradiator, the above-mentioned Cu board was irradiated with ultraviolet light.
(Ultraviolet Light Irradiation Conditions)
Ultraviolet ray irradiator: belt conveyor-type UV irradiator (manufactured by EYE GRAPHICS Co., Ltd.)
Lamp: 1.5 kW high-pressure mercury lamp
Irradiance (measured with a 365 nm head photometer): 100 mW/cm$^2$
Integral light dose (measured with a 365 nm head photometer): 1000 mJ/cm$^2$ After the irradiation, the composition was post-cured on a hot plate at 120° C. for 15 minutes to prepare a metal erosion test sample.

The sample was leaved to stand for 720 hours under hot and humid condition of 80° C./85%, and then a metal erosion test was performed. The existence of metal erosion about the after-tested board was visually evaluated. Evaluation criteria are as follows.
(Evaluation Criteria)
⊙: The color change of the Cu board was not found entirely by visual test.
○: The color change of the Cu board was found slight by visual test.
Δ: The Cu board was seen slight black by visual test.
x: The Cu board was changed pitch black.

TABLE 2

| No. | Photo-Curability | Heat Resistance (Yellowing) | Metal Errosion Resistance |
|---|---|---|---|
| 1 | ⊙ | ⊙ | ⊙ |
| 2 | ⊙ | ⊙ | ⊙ |
| 3 | ⊙ | ⊙ | ⊙ |
| 4 | ⊙ | ⊙ | ⊙ |
| 5 | ⊙ | ⊙ | ⊙ |
| 6 | ⊙ | ⊙ | ⊙ |
| 7 | ⊙ | ⊙ | ⊙ |
| 8 | ⊙ | ⊙ | ⊙ |
| 9 | ⊙ | ⊙ | ⊙ |
| 10 | ⊙ | ⊙ | ⊙ |
| 11 | ⊙ | ⊙ | ⊙ |
| 12 | ⊙ | ⊙ | ⊙ |
| 13 | ⊙ | ⊙ | ⊙ |
| 14 | ⊙ | ⊙ | ⊙ |
| 15 | ⊙ | ⊙ | ⊙ |
| 16 | ⊙ | ⊙ | ⊙ |
| 17 | ⊙ | ⊙ | ⊙ |
| 18 | ⊙ | ⊙ | ⊙ |
| 19 | ⊙ | ⊙ | ⊙ |
| 20 | ⊙ | ⊙ | ⊙ |
| 21 | ⊙ | ⊙ | ⊙ |
| 22 | ⊙ | ⊙ | ⊙ |
| 23 | ⊙ | ⊙ | ⊙ |
| 24 | ⊙ | ⊙ | ⊙ |
| 25 | ⊙ | ⊙ | ⊙ |
| 26 | ⊙ | ⊙ | ⊙ |
| 27 | ⊙ | ⊙ | ⊙ |
| 28 | ⊙ | ⊙ | ⊙ |
| 29 | ⊙ | ⊙ | ⊙ |
| 30 | ⊙ | ⊙ | ⊙ |
| 31 | ⊙ | ⊙ | ⊙ |
| 32 | ⊙ | ⊙ | ⊙ |
| 33 | ⊙ | ⊙ | ⊙ |
| 34 | ⊙ | ⊙ | ⊙ |
| 35 | ⊙ | ⊙ | ⊙ |
| 36 | ⊙ | ⊙ | ⊙ |
| 37 | ⊙ | ⊙ | ⊙ |
| 38 | ⊙ | ⊙ | ⊙ |
| 39 | ⊙ | ⊙ | ⊙ |
| 40 | ⊙ | ⊙ | ⊙ |
| 41 | ⊙ | ⊙ | ⊙ |
| 42 | ⊙ | ⊙ | ⊙ |
| 43 | ⊙ | ⊙ | X |
| 44 | ⊙ | X | ○ |
| 45 | X | ⊙ | X |

<Heatsensitivity (Heat-Curability) Evaluation>

The heat-curable compositions 35 to 42 of the present invention and comparative heat-curable compositions 46 to 48 obtained above were applied onto a slide glass with a thickness of 40 μm by an applicator. After the application, the composition was heated on a hot plate at 120° C. for 5 minutes, and then the pencil hardness (JIS K 5600-5-4: 1999) of the coating film hardness immediately after heating was measured and evaluated according to the criteria below (the coating film had a thickness of about 40 m after the curing).
(Evaluation Criteria)
⊙: The pencil hardness is 2H or higher.
○: The pencil hardness is from H to B.
Δ: The pencil hardness is from 2B to 4B.
x: Due to liquidness or tackiness, it is not possible to measure the pencil hardness.
<Heat Resistance (Yellowing) Test-2>

The heat-curable compositions 35 to 43 of the present invention and comparative heat-curable compositions 46 to 48 obtained above were applied onto a slide glass with a thickness of 40 μm by an applicator.

The sample was heated for 15 minutes on a hot plate controlled to a temperature of 240° C., and cured. The color of the coating film was visually evaluated. Evaluation criteria are as follows.
(Evaluation Criteria)
⊙: Colorless (yellowing of coating film does not occur)
○: Pale yellow or yellow
x: Brown
<Metal Erosion Test>

The heat-curable compositions 35 to 42 of the present invention and comparative heat-curable compositions 46 to 48 obtained above were applied onto Cu board with a thickness of 40 μm by an applicator. After the application, the composition was heated on a hot plate at 120° C. for 5 minutes, and cured.

The sample was leaved to stand for 720 hours under hot and humid condition of 80° C./85%, and then a metal erosion test was performed. The existence of metal erosion about the after-tested board was visually evaluated. Evaluation criteria are as follows.

(Evaluation Criteria)

⊙: The color change of the Cu board was not found entirely by visual test.

◯: The color change of the Cu board was found slight by visual test.

Δ: The Cu board was seen slight black by visual test.

x: The Cu board was changed pitch black.

TABLE 3

| No. | Heat-Curability | Heat Resistance (Yellowing) | Metal Errosion Resistance |
|---|---|---|---|
| 35 | ⊙ | ⊙ | ⊙ |
| 36 | ⊙ | ⊙ | ⊙ |
| 37 | ⊙ | ⊙ | ⊙ |
| 38 | ⊙ | ⊙ | ⊙ |
| 39 | ⊙ | ⊙ | ⊙ |
| 40 | ⊙ | ⊙ | ⊙ |
| 41 | ⊙ | ⊙ | ⊙ |
| 42 | ⊙ | ⊙ | ⊙ |
| 46 | ⊙ | ⊙ | X |
| 47 | ⊙ | X | ◯ |
| 48 | ◯ | ⊙ | X |

From the results in Tables 2 and 3, it is apparent that the curable composition containing an acid generator of the present invention are useful for members that are required to have optical properties, such as displays, optical waveguides and optical lenses, because favorable heat or UV curability is exhibited, a cured product has high transparency (hardly turns yellow) after a heat resistance test, and has excellent metal erosion resistance.

INDUSTRIAL APPLICABILITY

The curable composition of the present invention is suitably used for paints, coating agents, various coating materials (hard coats, anti-fouling coating materials, anti-fogging coating materials, anti-corrosion coating materials, optical fibers and the like), back surface treatment agents for adhesive tapes, release coating materials of release sheets for adhesive labels (release papers, release plastic films, release metal foils and the like), printing plates, ink compositions for dental materials (dental formulations and dental composites), ink compositions, inkjet ink compositions, positive resists (for formation of connection terminals and wiring patterns in production of electronic components such as circuit boards, CSP and MEMS elements), resist films, liquid resists and negative resists (permanent film materials of surface protecting films, interlayer dielectric films, planarizing films for semiconductor elements, and transparent electrode for FPD (ITO, IZO, GZO) etc.), resists for MEMS, positive photosensitive materials, negative photosensitive materials, various adhesives (various temporary fixing agents for electronic components, adhesives for HDD, adhesives for pick-up lenses, adhesives for functional films for FPD (polarizing plates, antireflection films), insulator films for circuit pattern and semiconductor sealing, anisotropic conductive adhesives (ACA), anisotropic conductive films (ACF) anisotropic conductive pastes (ACP) and the like), holographic resins, FPD materials (color filters, black matrices, partition wall materials, photospacers, ribs, orientation films for liquid crystals, sealing agents for FPD and the like), optical members, molding materials (for building materials, optical components and lenses), casting materials, putty materials, glass fiber impregnating agents, fillers, sealing materials, chip sealants (flip chip and COF), sealants for package (CSP or BGA), photosemiconductor (LED) sealing materials, optical waveguide materials, nano-imprint materials, stereolithography materials, and micro-stereolithography materials. Especially, the cured product obtained is most useful for materials of electronic components and circuit pattern.

The invention claimed is:

1. A sulfonium salt formed of a sulfonium cation and a gallate anion,
    the sulfonium cation being selected from the group consisting of

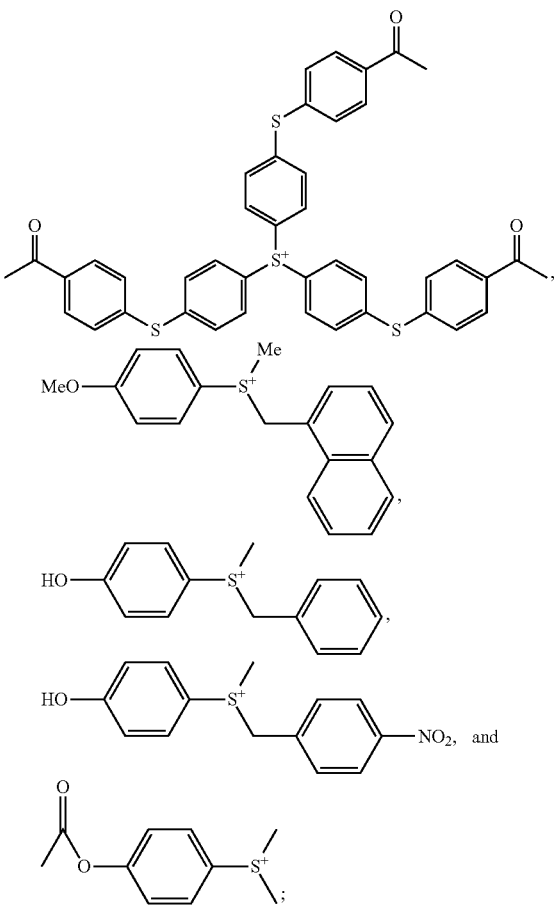

and
    the gallate anion being represented by $[Ga(C_6F_5)_4]^-$ or $[Ga((CF_3)_2C_6H_3)_4]^-$.

2. A heat- or photo-acid generator, comprising the sulfonium salt according to claim 1.

3. A heat- or energy ray-curable composition, comprising the heat- or photo-acid generator according to claim 2 and a cationic polymerizable compound.

4. A cured product obtained by curing the heat- or energy ray-curable composition according to claim 3.

* * * * *